US011707535B2

(12) United States Patent
Marsala et al.

(10) Patent No.: US 11,707,535 B2
(45) Date of Patent: Jul. 25, 2023

(54) METHOD AND COMPOSITION FOR TREATING NEUROPATHIC PAIN

(71) Applicant: The Regents of the University of California, Oakland, CA (US)

(72) Inventors: Martin Marsala, Solana Beach, CA (US); Atsushi Miyanohara, San Diego, CA (US); Takahiro Tadokoro, San Diego, CA (US)

(73) Assignee: The Regents of the University of California, Oakland, CA (US)

(*) Notice: Subject to any disclaimer, the term of this patent is extended or adjusted under 35 U.S.C. 154(b) by 621 days.

(21) Appl. No.: 16/638,972

(22) PCT Filed: Sep. 7, 2018

(86) PCT No.: PCT/US2018/049914
§ 371 (c)(1),
(2) Date: Feb. 13, 2020

(87) PCT Pub. No.: WO2019/051202
PCT Pub. Date: Mar. 14, 2019

(65) Prior Publication Data
US 2021/0353775 A1    Nov. 18, 2021

Related U.S. Application Data

(60) Provisional application No. 62/556,088, filed on Sep. 8, 2017.

(51) Int. Cl.
| | | |
|---|---|---|
| *A61K 48/00* | (2006.01) | |
| *A61K 35/761* | (2015.01) | |
| *A61K 38/17* | (2006.01) | |
| *A61K 38/51* | (2006.01) | |
| *A61K 9/00* | (2006.01) | |
| *A61P 25/02* | (2006.01) | |
| *A61P 25/04* | (2006.01) | |
| *C12N 15/86* | (2006.01) | |
| *C12N 7/00* | (2006.01) | |

(52) U.S. Cl.
CPC ........ *A61K 48/0058* (2013.01); *A61K 9/0019* (2013.01); *A61K 35/761* (2013.01); *A61K 38/1787* (2013.01); *A61K 38/51* (2013.01); *A61K 48/0025* (2013.01); *A61K 48/0075* (2013.01); *A61P 25/02* (2018.01); *A61P 25/04* (2018.01); *C12N 7/00* (2013.01); *C12N 15/86* (2013.01); *C12N 2750/14143* (2013.01); *C12N 2750/14171* (2013.01)

(58) Field of Classification Search
None
See application file for complete search history.

(56) References Cited

U.S. PATENT DOCUMENTS

| | | |
|---|---|---|
| 5,871,487 A | 2/1999 | Warner et al. |
| 8,292,874 B2 | 10/2012 | Stivland et al. |
| 9,827,109 B2 | 11/2017 | Steinberg |
| 10,688,285 B2 | 6/2020 | Marsala et al. |
| 2002/0082390 A1 | 6/2002 | Friddle et al. |
| 2003/0069398 A1 | 4/2003 | Rippmann et al. |
| 2003/0130577 A1 | 7/2003 | Purdy et al. |
| 2008/0051357 A1 | 2/2008 | Chang et al. |
| 2010/0030184 A1 | 2/2010 | Boulis et al. |
| 2012/0221063 A1 | 8/2012 | Abdou |
| 2013/0211380 A1 | 8/2013 | Aquino et al. |
| 2014/0058357 A1 | 2/2014 | Keyser et al. |
| 2014/0073684 A1 | 3/2014 | Stoffel et al. |
| 2014/0256801 A1 | 9/2014 | Glorioso et al. |
| 2015/0224331 A1 | 8/2015 | Marsala |
| 2015/0343038 A1 | 12/2015 | Marsala |
| 2016/0081956 A1 | 3/2016 | Kaufman et al. |
| 2018/0008727 A1 | 1/2018 | Marsala |
| 2018/0117282 A1 | 5/2018 | Marsala et al. |
| 2019/0071486 A1 | 3/2019 | Marsala |

FOREIGN PATENT DOCUMENTS

| | | |
|---|---|---|
| CA | 2998470 A1 | 3/2017 |
| CN | 101528922 A | 9/2009 |
| CN | 103328038 A | 9/2013 |
| JP | 6949867 B2 | 10/2021 |
| WO | 1994/10988 A | 5/1994 |
| WO | 2004/060464 A2 | 7/2004 |
| WO | WO-2008/010637 A1 | 1/2008 |
| WO | 2008/112177 A2 | 9/2008 |
| WO | 2010/071832 A1 | 6/2010 |
| WO | 2011/057171 A1 | 5/2011 |
| WO | 2012/075337 A2 | 6/2012 |
| WO | 2014/047540 A1 | 3/2014 |
| WO | 2014/116652 A2 | 7/2014 |

(Continued)

OTHER PUBLICATIONS

PCT/US2018/049914 International Search Report and Written Opinion dated Nov. 21, 2018.
"H.sapiens mRNA for glutamate decarboxylase, GenBank: X69936.1," GenBank, Mar. 16, 1993 [Retrieved from the Internet: https://www.ncbi.nlm.nih.gov/nuccore/X69936].
Egashira et al., "Unique pH dynamics in GABAergic synaptic vesicles illuminates the mechanism and kinetics of GABA loading" PNAS 113, Jul. 20, 2016, 10702-10707.
Extended European Search Report dated May 7, 2021, from application No. 18854448.0.

(Continued)

*Primary Examiner* — Robert M Kelly
(74) *Attorney, Agent, or Firm* — Foley & Lardner LLP

(57) ABSTRACT

The present invention provides a therapy for treating neuropathic pain by subpial administration of small quantities of a composition for spinal segment-specific upregulation of GAD65 (glutamatedecarboxylase) gene and VGAT (vesicular GABA transporter) gene, which is effective for induction of nociceptive effects by potentiating release of vesicular GABA from infected dorsal horn neurons into the synaptic cleft.

21 Claims, 14 Drawing Sheets

Specification includes a Sequence Listing.

(56) References Cited

FOREIGN PATENT DOCUMENTS

| WO | WO-2014/116652 A2 | 7/2014 |
|---|---|---|
| WO | 2014/184576 A2 | 11/2014 |
| WO | 2016/122791 A1 | 8/2016 |
| WO | 2017/172606 A1 | 10/2017 |
| WO | WO-2017/172606 A1 | 10/2017 |

OTHER PUBLICATIONS

Wojcik et al., "A Shared Vesicular Carrier Allows Synaptic Corelease of GABA and Glycine" Neuron 50, May 18, 2006, 575-587.
PCT/US2020/013059 International Search Report and Written Opinion dated Apr. 1, 2020.
Poston et al. "Catheter delivery systems for infusions into the cortex," Journal of Medical Engineering & Technology, Jul. 2011, 35(5):246-253.
Kantor et al. "Clinical Applications Involving CNS Gene Transfer," Adv Genet., 2014, 87:71-124.
Bouard et al. "Viral vectors: from virology to transgene expression," British Journal of Pharmacology, 2009, 157:153-165.
Adkins et al. "Tiagabine: A Review of its Pharmacodynamic and Pharmacokinetic Properties and Therapeutic Potential in the Management of Epilepsy," Drugs, Mar. 1998, 55(3):437-460.
Gholizadeh et al. "Transduction of the Central Nervous System After Intracerebroventricular Injection of Adeno-Associated Viral Vectors in Neonatal and Juvenile Mice," Human Gene Therapy Methods, Aug. 2013, 24:205-213.
EP14742941 Extended European Search Report dated Jun. 20, 2016.
Dayton et al. "The advent of AAV9 expands applications for brain and spinal cord gene delivery," Expert Opinion on Biological Therapy, Jun. 15, 2012, 12(6):757-766.
Federici et al. "Robust spinal motor neuron transduction following intrathecal delivery of AAV9 in pigs," Gene Therapy, 2012, 19(8):852-859.
Foust et al. "Intravascular AAV9 preferentially targets neonatal neurons and adult astrocytes," Nature Biotechnology, Jan. 2009, 27(1):59-65.
Hirai et al. "Intrathecal shRNA-AAV9 Inhibits Target Protein Expression in the Spinal Cord and Dorsal Root Ganglia of Adult Mice," Human Gene Therapy Methods, Apr. 1, 2012, 23(2):119-127.
Kakinohana et al. "Combinational Spinal GAD65 Gene Delivery and Systemic GABA-Mimetic Treatment for Modulation of Spasticity," Plos One, Jan. 2012, 7(1):e30561.
PCT/US2017/024285 International Search Report and Written Opinion dated Aug. 10, 2017.
Jin et al. "Demonstration of Functional Coupling between Gamma-Aminobutyric acid (GABA) Synthesis and Vesicular GABA Transport into Synaptic Vesicles," Proc Natl Acad Sci USA, Apr. 2003, 100(7):4293-4298.
EP15880645 Extended European Search Report dated May 24, 2018.
Colak et al. "Adenovirus-mediated gene therapy for experimental spinal cord tumors: tumoricidal efficacy and functional outcome," Brain Research, May 1995, 691:76-82.
JP2017-540569 Office Action dated Jun. 26, 2018.
PCT/US2015/065704 International Search Report dated Feb. 25, 2016.
CN201580078566.9 Office Action dated Sep. 24, 2019.
JP2017-540569 Office Action dated Jun. 4, 2019.
Bell et al. "Motor Neuron Transduction After Intracisternal Delivery of AAV9 in a Cynomolgus Macaque," Human Gene Therapy Methods, Apr. 2015, 26:43-44.
Duque et al. "Intravenous Administration of Self-complementary AAV9 Enables Transgene Delivery to Adult Motor Neurons," Molecular Therapy, Jul. 2009, 17(7):1187-1196.
Foust et al. "Therapeutic AAV9-mediated Suppression of Mutant SOD1 Slows Disease Progression and Extends Survival in Models of Inherited ALS," Molecular Therapy, Dec. 2013, 21(12):2148-2159.
Gray et al. "Preclinical Differences of Intravascular AAV9 Delivery to Neurons and Glia: A Comparative Study of Adult Mice and Nonhuman Primates," Molecular Therapy, Jun. 2011, 19(6):1058-1069.
Kakinohana et al. "Region-specific cell grafting into cervical and lumbar spinal cord in rat: a qualitative and quantitative stereological study," Experimental Neurology, 2004, 190:122-132.
Meyer et al. "Improving Single Injection CSF Delivery of AAV9-mediated Gene Therapy for SMA: A Dose-response Study in Mice and Nonhuman Primates," Molecular Therapy, Mar. 2015, 23(3):477-487.
Passini et al. "Translational Fidelity of Intrathecal Delivery of Self-Complementary AAV9-Survival Motor Neuron 1 for Spinal Muscular Atrophy," Human Gene Therapy, Jul. 2014, 25:619-630.
Usvald et al. "Analysis of Dosing Regimen and Reproducibility of Intraspinal Grafting of Human Spinal Stem Cells in Immunosuppressed Minipigs," Cell Transplantation, 2010, 19:1103-1122.
Xiao et al. "Production of High-Titer Recombinant Adeno-Associated Virus Vectors in the Absence of Helper Adenovirus," Journal of Virology, Mar. 1998, 72(3):2224-2232.
Xu et al. In Vivo Gene Knockdown in Rat Dorsal Root Ganglia Mediated by Self-Complementary Adeno-Associated Virus Serotype 5 Following Intrathecal Delivery, PLoS ONE, Mar. 2012, 7(3):e32581.
CN201580078566.9 Office Action dated Apr. 28, 2020.
EP17776384.4 Extended European Search Report dated Jul. 31, 2019.
Kitzman, Patrick. "Changes in vesicular glutamate transporter 2, vesicular GABA transporter and vesicular acetylcholine transporter labeling of sacrocaudal motoneurons in the spastic rat," Experimental Neurology, 2006, 197:407-419.
Bu et al. "Two human glutamate decarboxylases, 65-kDa GAD and 67-kDa GAD, are each encoded by a single gene," Proc. Natl. Acad. Sci. USA, Mar. 1992, 89:2115-2119.
Chaudhry et al. "The Vesicular GABA Transporter, VGAT, Localizes to Synaptic Vesicles in Sets of Glycinergic as Well as GABAergic Neurons," The Journal of Neuroscience, Dec. 1, 1998, 18(23):9733-9750.

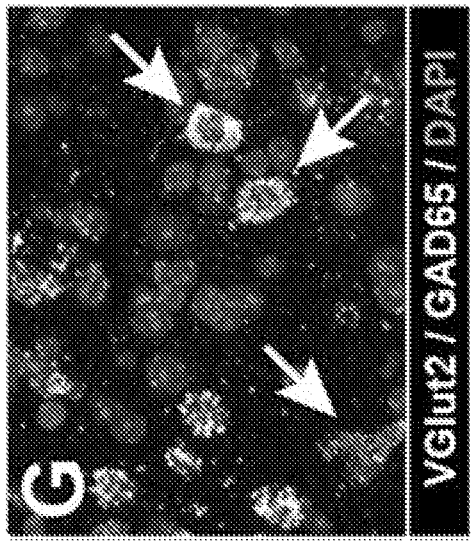
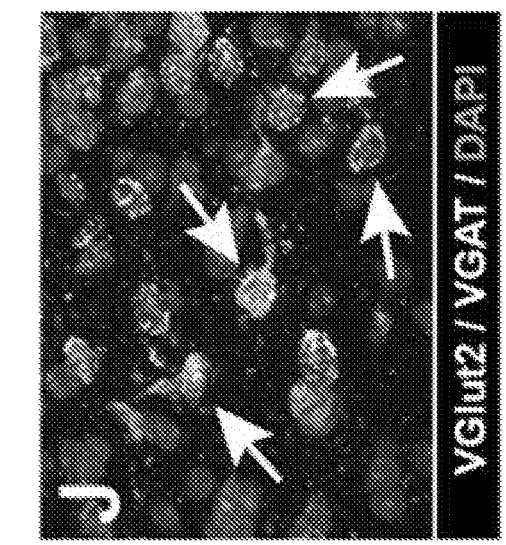
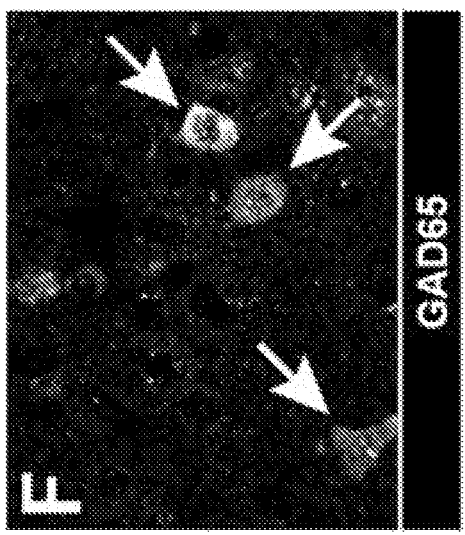
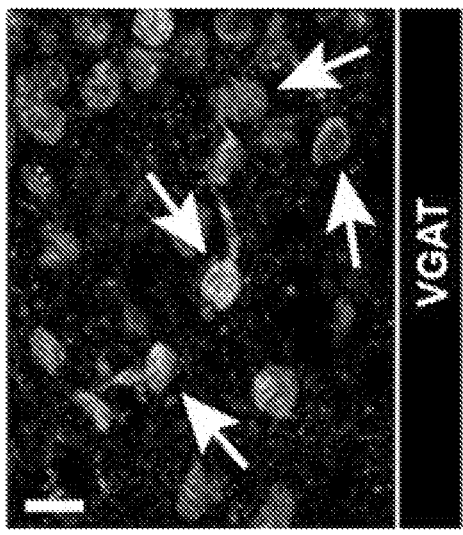
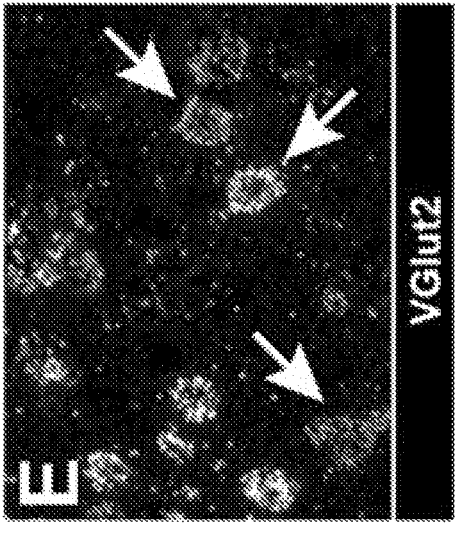
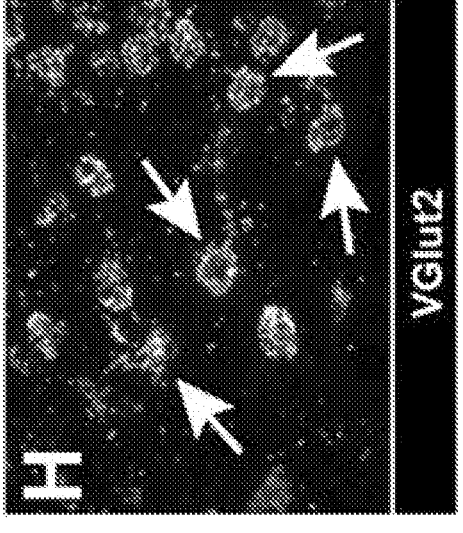

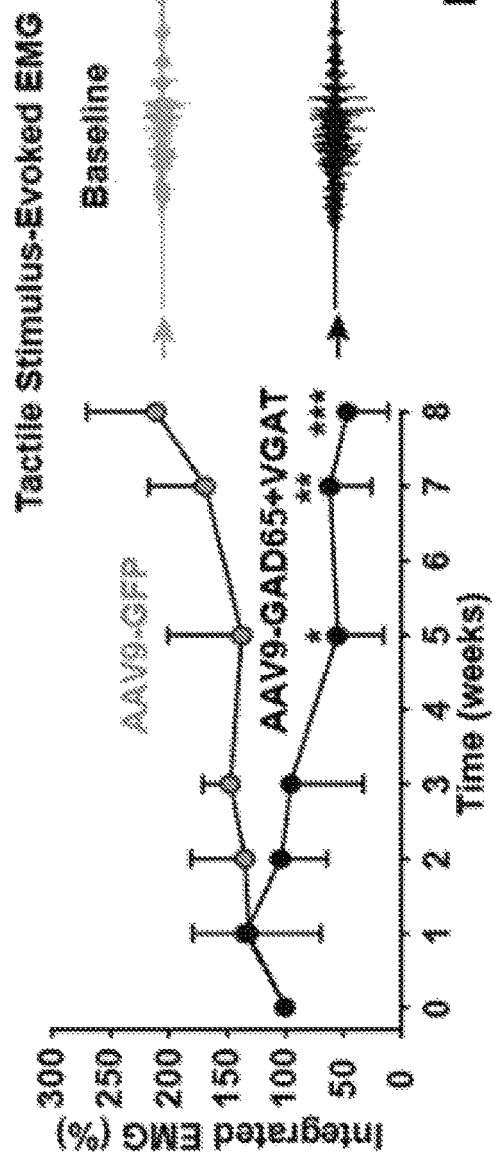
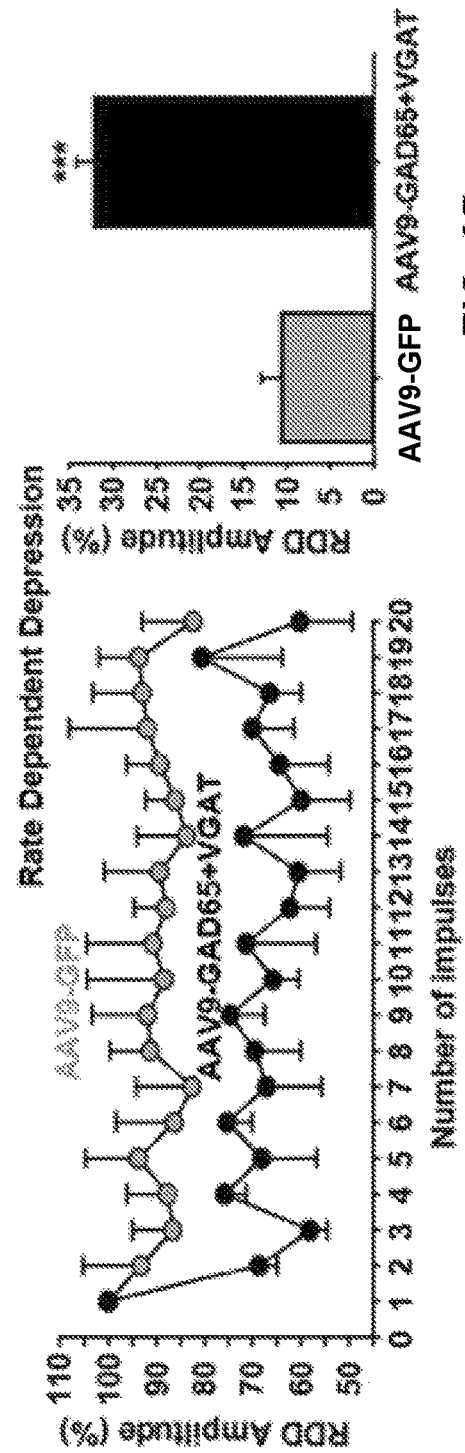
FIG. 8A
FIG. 8B
FIG. 8C
FIG. 8D

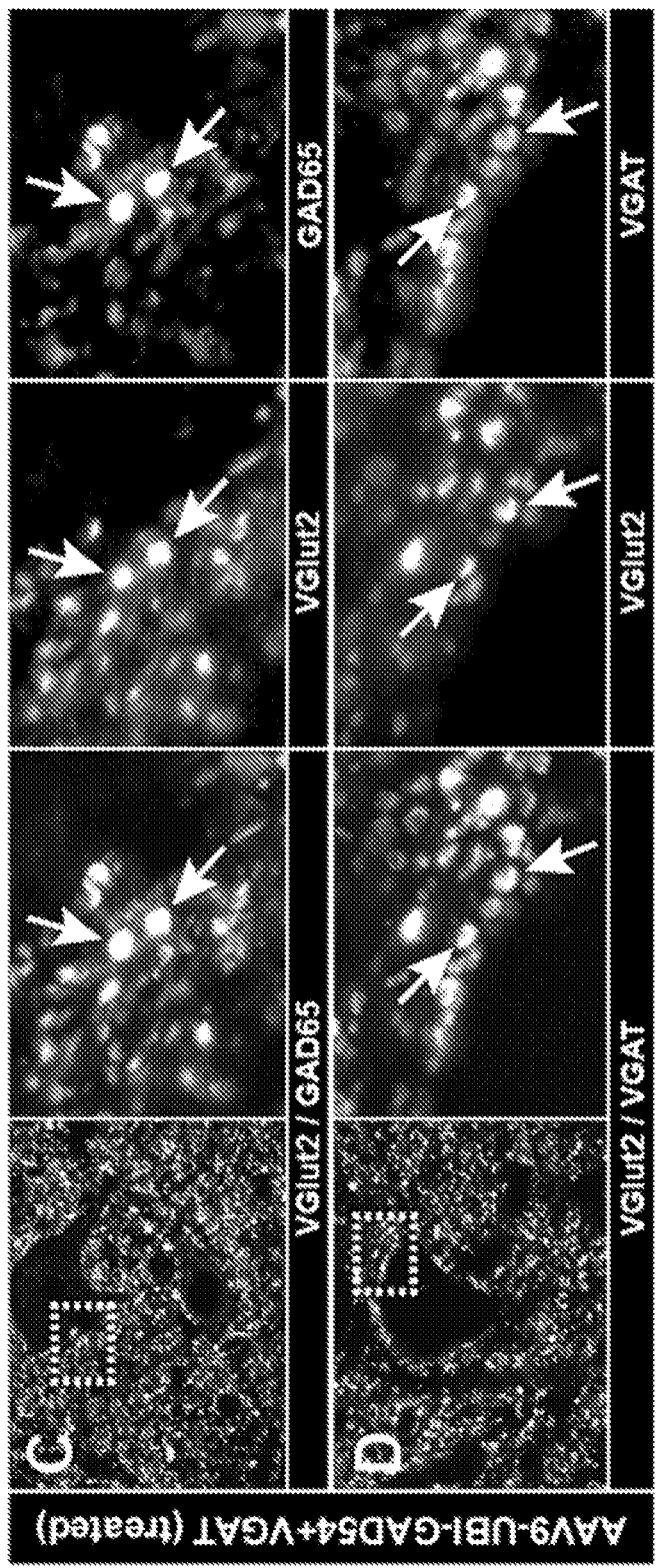

METHOD AND COMPOSITION FOR TREATING NEUROPATHIC PAIN

CROSS REFERENCE TO RELATED APPLICATION(S)

This application is a US national phase application under 35 U.S.C. § 371 of international patent application no. PCT/US2018/049914, filed Sep. 7, 2018, which claims the benefit of priority under 35 U.S.C. § 119(e) of U.S. Ser. No. 62/556,088, filed Sep. 8, 2017, the entire content of each of which is incorporated herein by reference.

SEQUENCE LISTING

The instant application contains a Sequence Listing which has been submitted electronically in ASCII format and is hereby incorporated by reference in its entirety. The ASCII copy, created on Sep. 6, 2018, is named 20378-201844_SL.txt and is 22 KB in size.

BACKGROUND OF THE INVENTION

Field of the Invention

The invention relates generally to treating neuropathic pain and more specifically to a combined therapeutic regimen involving spinal subpial delivery of one or more genes for treating chronic neuropathic pain.

Background Information

Neuropathic pain is pain caused by various types of nerve damage. Some examples of neuropathic pain conditions include, but are not limited to, diabetic peripheral neuropathy, herpes zoster, post herpetic neuralgia, trigeminal neuralgia, complex regional pain syndrome, reflex sympathetic dystrophy, migraine headache, phantom limb syndrome, neuropathic pain due to chronic disease (multiple sclerosis, HIV, etc), neuropathic pain due to trauma (causalgia), neuropathic pain due to impingement (i.e. sciatica, carpal tunnel, etc.), neuropathic pain due to drug exposure or toxic chemical exposure, neuropathic pain due to infection or post infection, neuropathic pain due to impaired organ function, neuropathic pain due to vascular disease, neuropathic pain due to metabolic disease, neuropathic pain due to cancer or cancer treatment, neuropathic pain due to autoimmune disease, neuropathic low back pain, neuropathic pain due to fibromylagia, and neuropathic pain with no known cause (idiopathic). In fact, neuropathic pain is most often diagnosed based on the symptoms, so that any pain is that is characterized by burning sensations and/or shooting pain and/or numbness and/or tingling and/or allodynia is typically considered neuropathic. Other characteristics of neuropathic pain include hyperpathia (greatly exaggerated pain sensation to stimuli), hyperesthesia (an increased sensitivity to normal stimulation), dysesthesia (unpleasant abnormal sensations as if damage is being done when this is not the case), and paresthesia (an abnormal sensation, such as "pins and needles", whether spontaneous or evoked).

It is well known that nociceptive pain and neuropathic pain are caused by different mechanisms, and therefore respond to different treatment modalities. Nociceptive pain is mediated by receptors which are located in skin, bone, connective tissue, muscle and viscera. These receptors typically respond to noxious chemical, thermal and mechanical stimuli producing pain that is typically described as sharp, aching, throbbing, or gnawing. In contrast, neuropathic pain is produced by damage to, or pathological changes in, the peripheral or central nervous systems, typically producing pain that is described as "burning", "electric", "tingling", and "shooting" in nature. Finally, nociceptive pain usually responds to opioids and non-steroidal anti-inflammatories (NSAIDS), whereas success treating neuropathic pain with these approaches has been limited.

At present, intrathecally-infused anti-nociceptive compounds (like gabapentin and opioids) are used to achieve a spinally-restricted anti-nociceptive effect. However, no gene-therapy-based technique is available to treat chronic neuropathic pain. Similarly, no gene therapy-based technique that can effectively be used to suppress nociceptive transmission in specific spinal segments, and which is ipsilateral to the site of peripheral nerve injury, is currently available. In addition, currently available spinal drug delivery systems (such as epidural or intrathecal delivery) do not permit a spinal segment-restricted therapeutic effect. Thus, a need exists for such improved treatments for neuropathic pain.

SUMMARY OF THE INVENTION

The present invention is based on the observation that a combined treatment composed of spinal segment-specific upregulation of GAD65 (glutamatedecarboxylase) and VGAT (vesicular GABA transporter) is effective for induction of nociceptive effects by potentiating release of vesicular GABA from infected dorsal horn neurons into the synaptic cleft.

Accordingly, the invention provides a method of treating neuropathic pain in a subject. The method includes subpial administration of a composition comprising: (i) a viral vector sequence, a GAD65 gene sequence (e.g., SEQ ID NO: 2 or 5), and a VGAT gene sequence (e.g., SEQ ID NO: 4 or 6) under the control of a tissue-specific promoter; and (ii) a pharmaceutically acceptable viral carrier, thereby treating neuropathic pain in the subject. In various embodiments, the subject may be a mammal. In various embodiments, the nucleic acid construct is encapsidated with an AAV serotype 9 capsid. In various embodiments, the concentration of the nucleic acid construct in the composition is between about $0.1$-$2.0\times10^{13}$ gc/ml. In various embodiments, the pharmaceutically acceptable viral carrier is selected from the group consisting of a lentiviral vector, an adenoviral vector (AV), or an adeno-associated vector (AAV). In various embodiments, the AAV is selected from the group consisting of AAV2, AAV3, AAV4, AAV5, AAV6, AAV7, AAV8, AAV9, AAV rh8, AAVrh10, AAVrh33, AAV rh34, and AAV Anc80. In various embodiments, the tissue-specific promoter is selected from the group consisting of human ubiquitin promoter and human synapsin promoter.

In another aspect, the invention provides a method of treating neuropathic pain in a subject. The method includes subpially administering a composition comprising a therapeutically effective amount of a gene therapy construct comprising (i) a viral vector sequence; (ii) a GAD65 gene sequence; and (iii) a VGAT gene sequence under control of a tissue-specific promoter, and a pharmaceutically acceptable carrier, thereby treating neuropathic pain in the subject. In various embodiments, the nucleic acid construct is encapsidated with an AAV serotype 9 capsid. In various embodiments, the concentration of the nucleic acid construct in the composition is between about $0.1$-$2.0\times10^{13}$ gc/ml. In various embodiments, the pharmaceutically acceptable viral carrier is selected from the group consisting of a lentiviral vector, an adenoviral vector (AV), or an adeno-associated vector (AAV). In various embodiments, the AAV is selected from the group consisting of AAV2, AAV3, AAV4, AAV5, AAV6, AAV7, AAV8, AAV9, AAV rh8, AAVrh10, AAVrh33, AAV rh34, and AAV Anc80. In various embodiments, the tissue-specific promoter is selected from the group consisting of human ubiquitin promoter and human synapsin promoter.

In another aspect, the invention provides a method of treating neuropathic pain in a subject. The method includes subpial administration of a first vector encoding GAD65 (glutamate decarboxylase) gene and a second vector encoding VGAT (vesicular GABA transporter) gene, thereby treating neuropathic pain in the subject. Administration of the first and second vectors results in spinal-specific upregulation of the GAD65 gene and VGAT gene in the subject. In various embodiments, the first viral vector comprises a polynucleotide encoding GAD65 and the second viral vector comprises a polynucleotide encoding VGAT, wherein GAD65 and VGAT are expressed in the subject, thereby treating neuropathic pain in the subject. The first and second vectors may be a lentiviral vector, adenoviral vector, or an adeno-associated vector (AAV). The AAV may be AAV type 9 (AAV9) or AAV Anc80. In various embodiments, the first vector AAV9-UBI-GAD65 and the second vector is AAV9-UBI-VGAT.

In another aspect, the invention provides a method of treating neuropathic pain in a subject. The method includes subpially administering to a subject in need thereof a therapeutically effective amount of a viral vector comprising a polynucleotide encoding GAD65 and systemically administering to the subject a GABA agonist, thereby treating spasticity in the subject. The vector may be a lentiviral vector, adenoviral vector, or an adeno-associated vector (AAV), and may be administered directly into the spine of the subject. The AAV may be AAV type 9 (AAV9) or AAV Anc80. In various embodiments, the vector is AAV9-UBI-GAD65.

In another aspect, the invention provides a nucleic acid construct comprising: a viral vector sequence, a GAD65 gene sequence, and a VGAT gene sequence under the control of a tissue-specific promoter. In various embodiments, the tissue-specific promoter is selected from the group consisting of human ubiquitin promoter and human synapsin promoter. In various embodiments, the viral vector is an adeno-associated viral (AAV) vector, such as, AAV2, AAV3, AAV4, AAV5, AAV6, AAV7, AAV8, AAV9, AAV rh8, AAVrh10, AAVrh33, AAV rh34, or AAV Anc80.

BRIEF DESCRIPTION OF THE DRAWINGS

FIG. 1A shows a pictorial diagram of a spinal cord with a subpially placed catheter in an animal model. FIG. 1B shows unilateral subpial advancement (3 mm) of an injection needle into the subpial space for delivery of the vector composition. FIG. 1C shows unilateral dorsal horn mRNA-GFP signal (fluorescence in situ hybridization; FISH) at 2 weeks after unilateral subpial delivery of AAV9-UBI-GFP (0.5 µl; $1.2 \times 10^{13}$ gc/ml) in an adult mouse.

FIGS. 2A and 2B show significant suppression of tactile and brush-evoked nociceptive response in hind paw in animals receiving unilateral subpial injection of the AAV9-UBI-GAD65/VGAT vector. FIGS. 2C and 2D show significant improvement of open field motor performance (running distance) and ipsilateral hind paw placement pattern (Cat Walk assay) in neuropathic animals receiving unilateral subpial injection of the AAV9-UBI-GAD65/VGAT vector. FIGS. 2E and 2F show that a comparable anti-nociceptive effect was seen in neuropathic animals treated with the Anc80-UBI-GAD65/VGAT vector.

FIGS. 3A-3D show images of staining of ipsilateral dorsal horn neurons with VGLUT2 (FIG. 3A), GAD65 (FIG. 3B), VGAT (FIG. 3C) and colocalization of VGLUT2, GAD65 and VGAT-stained puncta (FIG. 3D). A clear co-expression of VGLUT2 with VGAT and VGLUT2 with GAD65 (white arrows) was detected. FIG. 3E shows quantitative densitometry results of VGLUT, GAD65 and VGAT expression in the dorsal horn (lamina I-III) in treated (Injured+GAD65+VGAT) and control (Injured+PBS) animals. Mice were injected ipsilaterally (L2-L4) with AAV9-UBI-GAD65/VGAT vector or PBS only. No increased expression in contralateral dorsal horn was seen/measured.

FIGS. 4E-4J are pictorial diagrams showing the results from fluorescence in situ hybridization that show a clear appearance of double and triple-tagged neurons (white arrows) with VGLUT2, GAD65 and VGAT mRNA in ipsilateral dorsal horn neurons in AAV9-UBI-GAD65/VGAT-injected animals.

FIGS. 8A-8D are pictorial and graphical diagrams showing anti-spasticity effect after subpial delivery of AAV9-UBI-GAD65/VGAT in chronic rat model of spinal transection-induced muscle spasticity. FIGS. 8A and 8B show the results of measurement of muscle spasticity in animals receiving a control vector (AAV9-GFP), which showed a progressive increase in muscle spasticity for 8 weeks after virus delivery (compared to baseline measured at 2-3 months after spinal transection). In contrast a near complete block of spasticity response was measured in animals receiving AAV9-UBI-GAD65/VGAT vector. FIGS. 8C and 8D show the results of measurement of rate-dependent depression (RDD) of H-reflex, which showed a significant recovery of RDD in animals treated with AAV9-UBI-GAD65/VGAT vector.

FIGS. 9A-9D are pictorial diagrams showing expression of VGLUT2, GAD65 and VGAT in dorsal horn neurons in animals (rats) injected with AAV9-UBI-GFP (control vector) or AAV9-UBI-GAD65/VGAT vector. FIGS. 9A and 9B show no co-expression of GAD65 and VGAT in VGLUT2 terminals in animals receiving control AAV9-UBI-GFP vector. FIGS. 9C and 9D show induction of mixed inhibitory-excitatory neurotransmitter phenotype in lumbar excitatory interneurons after bilateral (L2-L4) subpial AAV9-UBI-GAD65/VGAT delivery in an adult rat model of chronic muscle spasticity. The appearance of mixed neurotransmitter phenotype in spinal interneurons as evidenced by co-expression of GAD65 and VGAT in VGLUT2 terminals can be seen.

DETAILED DESCRIPTION OF THE INVENTION

Figure 1A:
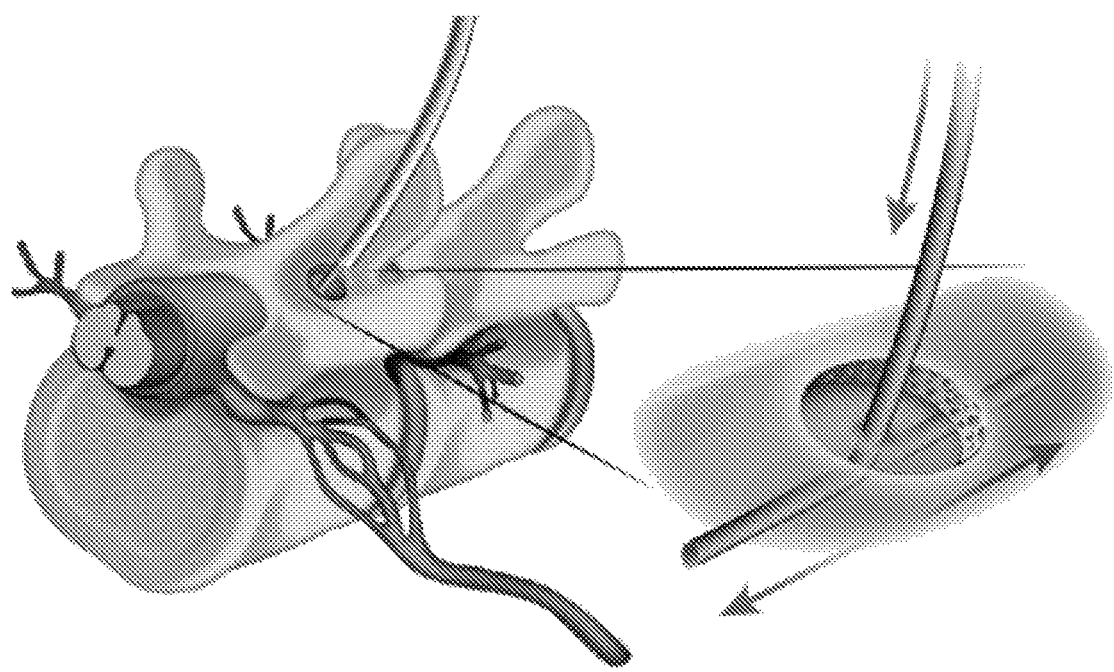
FIGS. 1A-1C are pictorial diagrams showing unilateral spinal subpial vector delivery.

The present invention is based on the observation that subpial administration of small quantities of a combined treatment composed of spinal segment-specific upregulation of GAD65 (glutamatedecarboxylase) gene and VGAT (vesicular GABA transporter) gene is effective for induction of nociceptive effects by potentiating release of vesicular GABA from infected dorsal horn neurons into the synaptic cleft.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

The term "comprising," which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

The terms "about" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 10- or 5-fold, and more preferably within 2-fold of a given value. Numerical quantities given herein are approximate unless stated otherwise, meaning that the term "about" or "approximately" can be inferred when not expressly stated Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

The term "subject" as used herein refers to any individual or patient to which the subject methods are performed. Generally the subject is human, although as will be appreciated by those in the art, the subject may be an animal. Thus other animals, including mammals such as rodents (including mice, rats, hamsters and guinea pigs), cats, dogs, rabbits, farm animals including cows, horses, goats, sheep, pigs, etc., and primates (including monkeys, chimpanzees, orangutans and gorillas) are included within the definition of subject.

A "therapeutic effect," as used herein, encompasses a therapeutic benefit and/or a prophylactic benefit as described herein.

As used herein, the terms "reduce" and "inhibit" are used together because it is recognized that, in some cases, a decrease can be reduced below the level of detection of a particular assay. As such, it may not always be clear whether the expression level or activity is "reduced" below a level of detection of an assay, or is completely "inhibited." Nevertheless, it will be clearly determinable, following a treatment according to the present methods.

As used herein, "treatment" or "treating" means to administer a composition to a subject or a system with an undesired condition. The condition can include a disease or disorder. "Prevention" or "preventing" means to administer a composition to a subject or a system at risk for the condition. The condition can include a predisposition to a disease or disorder. The effect of the administration of the composition to the subject (either treating and/or preventing) can be, but is not limited to, the cessation of one or more symptoms of the condition, a reduction or prevention of one or more symptoms of the condition, a reduction in the severity of the condition, the complete ablation of the condition, a stabilization or delay of the development or progression of a particular event or characteristic, or minimization of the chances that a particular event or characteristic will occur.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, α-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

As used herein, a "regulatory gene" or "regulatory sequence" is a nucleic acid sequence that encodes products (e.g., transcription factors) that control the expression of other genes.

As used herein, a "protein coding sequence" or a sequence that encodes a particular protein or polypeptide, is a nucleic acid sequence that is transcribed into mRNA (in the case of DNA) and is translated (in the case of mRNA) into a polypeptide in vitro or in vivo when placed under the control of appropriate regulatory sequences. The boundaries of the coding sequence are determined by a start codon at the 5' terminus (N-terminus) and a translation stop nonsense codon at the 3' terminus (C-terminus). A coding sequence can include, but is not limited to, cDNA from eukaryotic mRNA, genomic DNA sequences from eukaryotic DNA, and synthetic nucleic acids. A transcription termination sequence will usually be located 3' to the coding sequence.

As used herein, a "promoter" is defined as a regulatory DNA sequence generally located upstream of a gene that mediates the initiation of transcription by directing RNA polymerase to bind to DNA and initiating RNA synthesis. A promoter can be a constitutively active promoter (i.e., a promoter that is constitutively in an active/"ON" state), it may be an inducible promoter (i.e., a promoter whose state, active/"ON" or inactive/"OFF", is controlled by an external stimulus, e.g., the presence of a particular compound or protein), it may be a spatially restricted promoter (i.e., transcriptional control element, enhancer, etc.) (e.g., tissue specific promoter, cell type specific promoter, etc.), and it may be a temporally restricted promoter (i.e., the promoter is in the "ON" state or "OFF" state during specific stages of embryonic development or during specific stages of a biological process.

As used herein, the term "gene" means the deoxyribonucleotide sequences comprising the coding region of a structural gene. A "gene" may also include non-translated sequences located adjacent to the coding region on both the 5' and 3' ends such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene which are transcribed into heterogenous nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the terms "functionally linked" and "operably linked" are used interchangeably and refer to a functional relationship between two or more DNA segments, in particular gene sequences to be expressed and those sequences controlling their expression. For example, a promoter/enhancer sequence, including any combination of cis-acting transcriptional control elements is operably linked to a coding sequence if it stimulates or modulates the transcription of the coding sequence in an appropriate host cell or other expression system. Promoter regulatory sequences that are operably linked to the transcribed gene sequence are physically contiguous to the transcribed sequence.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill in the art will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

A conservative substitution may include substitution such as basic for basic, acidic for acidic, polar for polar, etc. The sets of amino acids thus derived are likely to be conserved for structural reasons. These sets can be described in the form of a Venn diagram (Livingstone C. D. and Barton G. J. (1993) "Protein sequence alignments: a strategy for the hierarchical analysis of residue conservation" Comput. Appl Biosci. 9: 745-756; Taylor W. R. (1986) "The classification of amino acid conservation" J. Theor. Biol. 119; 205-218). Conservative substitutions may be made, for example, according to the table below which describes a generally accepted Venn diagram grouping of amino acids.

TABLE 1

Grouping of amino acids

| Character-istic | Set | Character-istic | Sub-set |
|---|---|---|---|
| Hydrophobic | F W Y H K M I L V A G C | Aromatic Aliphatic | F W Y H I L V |
| Polar | W Y H K R E D C S T N Q | Charged Positive | H K R E D H K R |
|  |  | Charged Negative | E D |
| Small | V C A G S P T N D | Tiny | A G S |

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (e.g., a polypeptide of the invention), which does not comprise additions or deletions, for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same sequences. Two sequences are "substantially identical" if two sequences have a specified percentage of amino acid residues or nucleotides that are the same (i.e., 60% identity, optionally 65%, 70%, 75%, 80%, 85%, 90%, or 95% identity over a specified region, or, when not specified, over the entire sequence), when compared and aligned for maximum correspondence over a comparison window, or designated region as measured using one of the following sequence comparison algorithms or by manual alignment and visual inspection. The invention provides polypeptides that are substantially identical to the polypeptides, respectively, exemplified herein, as well as uses thereof including, but not limited to, use for treating or preventing neurological diseases or disorders, e.g., neurodegenerative diseases or disorders, and/or treating SCI. Optionally, the identity exists over a region that is at least about 50 nucleotides in length, or more preferably over a region that is 100 to 500 or 1000 or more nucleotides in length, or the entire length of the reference sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch (1970) J. Mol. Biol. 48:443, by the search for similarity method of Pearson and Lipman (1988) Proc. Nat'l. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., Current Protocols in Molecular Biology (1995 supplement)).

Two examples of algorithms that are suitable for determining percent sequence identity and sequence similarity are the BLAST and BLAST 2.0 algorithms, which are described in Altschul et al. (1977) Nuc. Acids Res. 25:3389-3402, and Altschul et al. (1990) J. Mol. Biol. 215:403-410, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) Proc. Natl. Acad. Sci. USA 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) Proc. Natl. Acad. Sci. USA 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

"Nucleic acid" refers to deoxyribonucleotides or ribonucleotides and polymers thereof in either single- or double-stranded form, and complements thereof. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). In various embodiments, nucleic acids are isolated when purified away from other cellular components or other contaminants (e.g., other nucleic acids or proteins present in the cell) by standard techniques including, including alkaline/SDS treatment, CsCl banding, column chromatography, agarose gel electrophoresis and others well-known in the art. See e.g., F. Ausubel, et al., ed. (1987) Current Protocols in Molecular Biology, Greene Publishing and Wiley Interscience, New York. In various embodiments, a nucleic acid is, for example, DNA or RNA and may or may not contain intronic sequences. In a preferred embodiment, the nucleic acid is a cDNA molecule.

As used herein, a "vector" is a nucleic acid molecule that when introduced into a host cell produces a transformed host cell. A vector may include nucleic acid sequences that permit it to replicate in the host cell, such as an origin of replication. A vector may also include one or more selectable marker genes and other genetic elements known in the art. A vector may include a "gene transfer vector," "gene therapy vector," or "gene therapy construct," or similar terms, which refer to specific vector constructs that are suitable to conduct gene transfer to administer a desired gene.

The terms "vector," "cloning vector," and "expression vector" therefore refer to the vehicle by which a DNA or RNA sequence (e.g., a foreign gene) can be introduced into a host cell so as to transform the host and promote expression (e.g., transcription and translation) of the introduced sequence. Vectors include any genetic element, such as a plasmid, phage, transposon, cosmid, chromosome, virus, virion, etc., which is capable of replication when associated with the proper control elements and which can transfer gene sequences between cells. Thus, the term includes cloning and expression vehicles, as well as viral vectors.

As used herein "pharmaceutically acceptable carrier" encompasses any of the standard pharmaceutical carriers, such as a phosphate buffered saline solution, water and emulsions such as an oil/water or water/oil emulsion, and various types of wetting agents. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Suitable pharmaceutical carriers are described in Remington's Pharmaceutical Sciences, Mack Publishing Company, a standard reference text in this field.

As used herein, the term "gene therapy" refers to a method of changing the expression of an endogenous gene by exogenous administration of a gene, i.e., a GAD65 and/or VGAT gene. As used herein, gene therapy also refers to the replacement of a defective GAD65 and/or VGAT gene, or replacement of a missing GAD65 and/or VGAT gene, by introducing a functional gene or portion of a gene corresponding to the defective or missing GAD65 and/or VGAT gene into the spinal subpial space of an individual in need. For purposes of the present disclosure, gene therapy can be accomplished by "in vivo" methods using a broad range of viral vectors (e.g., AAV), liposomes, nanoparticles, protein: DNA complexes, modified nucleic acids or naked DNA in order to achieve a therapeutic outcome.

The term "transgene" refers to a polynucleotide that is introduced into a cell of a subject and is capable of being expressed under appropriate conditions and confers a desired property to a cell into which it was introduced, or otherwise leads to a desired therapeutic outcome.

The terms "genome particles (gp)," "genome equivalents," or "genome copies (gc)" as used in reference to a viral titer, refer to the number of virions containing the recombinant AAV DNA genome, regardless of infectivity or functionality. The number of genome particles in a particular vector preparation can be measured by procedures such as described elsewhere herein, or for example, in Clark et al. (1999) Hum. Gene Ther., 10:1031-1039; Veldwijk et al. (2002) Mol. Ther., 6:272-278.

As used herein, the term "neuron" include a neuron and a portion or portions thereof (e.g., the neuron cell body, an axon, or a dendrite). Thus, the term "neuron" as used herein denotes nervous system cells that include a central cell body or soma, and two types of extensions or projections: dendrites, by which, in general, the majority of neuronal signals are conveyed to the cell body, and axons, by which, in general, the majority of neuronal signals are conveyed from the cell body to effector cells, such as target neurons or muscle. Neurons can convey information from tissues and organs into the central nervous system (afferent or sensory neurons) and transmit signals from the central nervous systems to effector cells (efferent or motor neurons). Other neurons, designated interneurons, connect neurons within the central nervous system (the brain and spinal column). Certain specific examples of neuron types that may be subject to treatment or methods according to the invention include cerebellar granule neurons, dorsal root ganglion neurons, and cortical neurons.

The term "neuronal degeneration" is used broadly and refers to any pathological changes in neuronal cells, including, without limitation, death or loss of neuronal cells, any changes that precede cell death, and any reduction or loss of an activity or a function of the neuronal cells. The pathological changes may be spontaneous or may be induced by any event and include, for example, pathological changes associated with apoptosis. The neurons may be any neurons, including without limitation sensory, sympathetic, parasympathetic, or enteric, e.g., dorsal root ganglia neurons, motor neurons, and central neurons, e.g., neurons from the spinal cord. Neuronal degeneration or cell loss is a characteristic of a variety of neurological diseases or disorders, e.g., neurodegenerative diseases or disorders. In some embodiments, the neuron is a sensory neuron. In some embodiments, the neuron is a motor neuron. In some embodiments, the neuron is a damaged spinal cord neuron.

As used herein, "neurodegenerative disorder" or a "neurological disorder" refers to a disorder which causes morphological and/or functional abnormality of a neural cell or a population of neural cells. The neurodegenerative disorder can result in an impairment or absence of a normal neurological function or presence of an abnormal neurological function in a subject. For example, neurodegenerative disorders can be the result of disease, injury, and/or aging. Non-limiting examples of morphological and functional abnormalities include physical deterioration and/or death of neural cells, abnormal growth patterns of neural cells, abnormalities in the physical connection between neural cells, under- or over production of a substance or substances, e.g., a neurotransmitter, by neural cells, failure of neural cells to produce a substance or substances which it normally produces, production of substances, e.g., neurotransmitters, and/or transmission of electrical impulses in abnormal patterns or at abnormal times. Neurodegeneration can occur in any area of the brain of a subject and is seen with many disorders including, for example, head trauma, stroke, ALS, multiple sclerosis, Huntington's disease, Parkinson's disease, and Alzheimer's disease.

As used herein, the term "nociception" refers to the sensory nervous system's response to certain harmful or potentially harmful stimuli. In nociception, intense chemical (e.g., chili powder in the eyes), mechanical (e.g., cutting, crushing), or thermal (heat and cold) stimulation of sensory nerve cells called nociceptors produces a signal that travels along a chain of nerve fibers via the spinal cord to the brain. Nociception triggers a variety of physiological and behavioral responses and usually results in a subjective experience of pain in sentient beings.

Gamma-aminobutyric acid (GABA) and glutamate are the primary inhibitory and excitatory neurotransmitters in mammals. The balance between GABA and glutamate controls diverse processes such as neurogenesis, movement, circadian clocks, tissue development and blood glucose regulation. GABA is synthesized from glutamate by the 65 kDa and 67 kDa isoforms of the pyridoxal phosphate (PLP) dependent enzyme Glutamic Acid Decarboxylase (GAD65 and GAD67, respectively).

Nucleic acid sequences for rat GAD2/GAD65 are known in the art. See, for example, GenBank Accession No.: NM_012563, *Rattus norvegicus* glutamate decarboxylase 2 (Gad2), mRNA, which provides the nucleic acid sequence (SEQ ID NO: 5):

```
  1 gggcgtgcgg ggtcgagccg aagcagcttg
    cccgcagcca ctcggaggcg accagcgcca
 61 gactagcaga acccatggca tctccgggct
    ctggcttttg gtccttcgga tctgaagatg
121 gctctgggga tcctgagaac ccgggaacag
    cgagagcctg gtgccaggtg gcccaaaagt
181 tcacgggcgg catcggaaac aagctatgcg
    ctctgctcta cggagactct gagaagccag
241 cagagagcgg cgggagcgtg acctcgcggg
    ccgccactcg gaaggtcgcc tgcacctgtg
301 accaaaaacc ctgcagctgc cccaaaggag
    atgtcaatta tgcacttctc cacgcaacag
361 acctgctgcc agcctgtgaa ggagaaaggc
    ccactctcgc atttctgcaa gatgtaatga
421 acattttgct tcagtacgtg gtgaaaagtt
    ttgatagatc aactaaagtg attgatttcc
481 attacccccaa tgagcttctt caagagtata
    attgggaatt ggcagaccaa ccgcaaaatc
541 tggaggaaat tttgacgcac tgccaaacaa
    ctctaaaata tgcgattaaa acagggcatc
601 cccgatattt taatcagctg tctaccggat
    tggatatggt tggattagca gcagattggt
661 tgacatcaac agcaaacacg aacatgttta
    cctatgagat cgcccctgta tttgtactac
721 tggaatatgt gacactaaag aaaatgagggg
    aaatcattgg ctggccagga ggctctggcg
781 atggaatctt ttctcctggt ggtgccatct
    ccaacatgta cgccatgctc attgcccgct
841 ataagatgtt tccagaagtc aaggaaaagg
    ggatggcggc ggtgcccagg ctcatcgcat
901 tcacgtcaga gcatagtcac tttttctctca
    agaagggagc tgcagccttg gggatcggaa
961 cagacagcgt gattctgatt aaatgtgatg
    agagagggaa aatgatccca tctgaccttg
```

```
1021 aaagaagaat ccttgaagtc aaacagaaag
     gatttgttcc tttcctggtg agtgccacag
1081 ctggaaccac tgtgtacggg gcttttgatc
     ctctcttggc tgtagctgac atctgcaaaa
1141 aatataagat ctggatgcat gtggatgctg
     cttggggtgg agggttactg atgtctcgga
1201 aacacaagtg gaagctgaac ggtgtggaga
     gggccaactc tgtgacatgg aatcccaca
1261 agatgatggg tgtccccttg caatgttcgg
     ctctcctggt cagagaggag ggactgatgc
1321 agagctgcaa ccagatgcat gcttcctacc
     tctttcagca agataagcac tatgacctgt
1381 cctatgacac gggagacaag gccttgcagt
     gtggacgcca cgtcgatgtc tttaaattat
1441 ggctcatgtg gagagcaaag gggactactg
     gatttgaagc tcacattgat aagtgtttgg
1501 agctggcaga gtatttatac aatatcatta
     aaaaccgaga aggatatgaa atggtgttcg
1561 atgggaagcc tcagcacaca aatgtctgct
     tctggttttgt acctcctagt ttgcgagttc
1621 tggaagacaa tgaagagaga atgagccgcc
     tctcaaaggt ggcgccagtg attaaagcca
1681 gaatgatgga gtatgggacc acaatggtca
     gctaccaacc cttaggagat aaggtcaact
1741 tcttccgcat ggtcatctca aaccctgcag
     caactcacca agacattgac ttcctcattg
1801 aagaaatcga acgcctggga caagatttgt
     aatcactttg ctcaccaaac tttcagttct
1861 ctaggtagac agctaagttg tcacaaactg
     tgtaaatgta tttgtagttt gttccagagt
1921 aattctattt ctatatcgtg gtgtcacagt
     agagtccagt ttaaaa.
```

Human GAD65 and GAD67 have been isolated and cloned by Bu et al. (1992) Proc Natl Acad Sci 89:2115-2119. Human GAD65 cDNA encodes a Mr 65,000 polypeptide, with 585 amino acid residues (Genbank Accession No. NM000818; M81882), Human GAD67 encodes a Mr 67,000 polypeptide, with 594 amino acid residues (Genbank Accession No. NM013445; M81883); each of which is incorporated herein by reference). See also, US Pub. No. 2016/0081956, incorporated herein by reference).

Additional nucleic acid and amino acid sequences for human GAD65 are known in the art. See, for example, GenBank Accession No.: Q05329, human Glutamate decarboxylase 2 (GAD2/GAD65), which provides the amino acid sequence (SEQ ID NO: 1):

```
MASPGSGFWSFGSEDGSGDSENPGTARAWCQVAQKFTGGI
GNKLCALLYGDAEKPAESGGSQPPRAAARKAACACDQKPC
SCSKVDVNYAFLHATDLLPACDGERPTLAFLQDVMNILLQ
YVVKSFDRSTKVIDFHYPNELLQEYNWELADQPQNLEEIL
MHCQTTLKYAIKTGHPRYFNQLSTGLDMVGLAADWLTSTA
NTNMFTYEIAPVFVLLEYVTLKKMREIIGWPGGSGDGIFS
PGGAISNMYAMMIARFKMFPEVKEKGMAALPRLIAFTSEH
SHFSLKKGAAALGIGTDSVILIKCDERGKMIPSDLERRIL
EAKQKGFVPFLVSATAGTTVYGAFDPLLAVADICKKYKIW
MHVDAAWGGGLLMSRKHKWKLSGVERANSVTWNPHKMMGV
PLQCSALLVREEGLMQNCNQMHASYLFQQDKHYDLSYDTG
DKALQCGRHVDVFKLWLMWRAKGTTGFEAHVDKCLELAEY
LYNIIKNREGYEMVFDGKPQHTNVCFWYIPPSLRTLEDNE
ERMSRLSKVAPVIKARMMEYGTTMVSYQPLGDKVNFFRMV
ISNPAATHQDIDFLIEEIERLGQDL.
```

See also, for example, GenBank Accession No.: X69936, *Homo sapiens* mRNA for glutamate decarboxylase (GAD2/GAD65), which provides the nucleic acid sequence (SEQ ID NO: 2):

```
  1 atgtcccta tacatcacca tcaccatcac
    ctggttccgc gtggatccga agcttcgaat
 61 tctggctttt ggtctttcgg gtcggaagat
    ggctctgggg attccgagaa tcccggcaca
121 gcgcgagcct ggtgccaagt ggctcagaag
    ttcacgggcg gcatcggaaa caaactgtgc
181 gccctgctct acggagacgc cgagaagccg
    gcggagagcg gcgggagcca accccgcgg
241 gccgccgccc ggaaggccgc ctgcgcctgc
    gaccagaagc cctgcagctg ctccaaagtg
301 gatgtcaact acgcgtttct ccatgcaaca
    gacctgctgc cggcgtgtga tggagaaagg
361 cccactttgg cgtttctgca agatgttatg
    aacatttac ttcagtatgt ggtgaaaagt
421 ttcgatagat caaccaaagt gattgatttc
    cattatccta atgagcttct ccaagaatat
481 aattgggaat tggcagacca accacaaaat
    ttggaggaaa ttttgatgca ttgccaaaca
541 actctaaaat atgcaattaa aacagggcat
    cctagatact tcaatcaact ttctactggt
601 ttggatatgg ttggattagc agcagactgg
    ctgacatcaa cagcaaatac taacatgttc
```

```
 661 acctatgaaa ttgctccagt atttgtgctt ttggaatatg tcacactaaa gaaaatgaga 721 gaaatcattg gctggccagg gggctctggc gatgggatat tttctcccgg tggcgccata 781 tctaacatgt atgccatgat gatcgcacgc tttaagatgt tcccagaagt caaggagaaa 841 ggaatggctg ctcttcccag gctcattgcc ttcacgtctg aacatagtca tttttctctc 901 aagaagggag ctgcagcctt agggattgga acagacagcg tgattctgat taaatgtgat 961 gagagaggga aaatgattcc atctgatctt gaaagaagga ttcttgaagc caaacagaaa 1021 gggtttgttc ctttcctcgt gagtgccaca gctggaacca ccgtgtacgg agcatttgac 1081 cccctcttag ctgtcgctga catttgcaaa aagtataaga tctggatgca tgtggatgca 1141 gcttggggtg ggggattact gatgtcccga aaacacaagt ggaaactgag tggcgtggag 1201 agggccaact ctgtgacgtg gaatccacac aagatgatgg gagtcccttt gcagtgctct 1261 gctctcctgg ttagagaaga gggattgatg cagaattgca accaaatgca tgcctcctac 1321 ctctttcagc aagataaaca ttatgacctg tcctatgaca ctggagacaa ggccttacag 1381 tgcggacgcc acgttgatgt ttttaaacta tggctgatgt ggagggcaaa ggggactacc 1441 gggtttgaag cgcatgttga taaatgtttg gagttggcag agtatttata caacatcata 1501 aaaaaccgag aaggatatga gatggtgttt gatgggaagc ctcagcacac aaatgtctgc 1561 ttctggtaca ttcctccaag cttgcgtact ctggaagaca atgaagagag aatgagtcgc 1621 ctctcgaagg tggctccagt gattaaagcc agaatgatgg agtatggaac cacaatggtc 1681 agctaccaac ccttgggaga caaggtcaat ttcttccgca tggtcatctc aaacccagcg 1741 gcaactcacc aagacattga cttcctgatt gaagaaatag aacgccttgg acaagattta 1801 taa.
```

GABA acts at inhibitory synapses in the brain by binding to specific transmembrane receptors in the plasma membrane of both pre- and postsynaptic neuronal processes. This binding causes the opening of ion channels to allow the flow of either negatively charged chloride ions into the cell or positively charged potassium ions out of the cell. This action results in a negative change in the transmembrane potential, usually causing hyperpolarization. Two general classes of GABA receptor are known: $GABA_A$ in which the receptor is part of a ligand-gated ion channel complex, and $GABA_B$ metabotropic receptors, which are G protein-coupled receptors that open or close ion channels via intermediaries (G proteins).

GABA agonists well known in the art include muscimol, progabide, riluzole, baclofen, gabapentin (NEURONTIN®), vigabatrin, valproic acid, tiagabine (GABITRIL®), lamotrigine (LAMICTAL®), pregabalin, phenytoin (DILANTIN®), carbamazepine (TEGRETOL®), topiramate (TOPAMAX®) and analogs, derivatives, prodrugs and pharmaceutically acceptable salts of those GABA agonists. It will be recognized by those skilled in the art that other GABA agonists are also useful in the combinations, pharmaceutical compositions, methods and kits of this invention. GABA agonists have been disclosed to be useful in anti-seizure therapy for central nervous system disorders such as epilepsy, Huntington's chorea, cerebral ischemia, Parkinson's disease, tardive dyskinesia and spasticity. GABA agonists have also been disclosed to be useful as antidepressants, anxiolytics, antipsychotics, and to have utility in the treatment of pain.

VGAT (vesicular GABA transporter) (also known as vesicular inhibitory amino acid transporter (VIAAT)) is a protein that in humans is encoded by the SLC32A1 gene (also known as the VGAT gene). VGAT is highly concentrated in the nerve endings of GABAergic neurons in the brain and spinal cord but also in glycinergic nerve endings. Caudhry, et al., J. Neurosci., 18(23):9733-9750 (1998), incorporated herein by reference. Nucleic acid and amino acid sequences for human VGAT are known in the art. See, for example, GenBank Accession No.: Q9H598, human Vesicular inhibitory amino acid transporter (VIAAT/VGAT), which provides the amino acid sequence (SEQ ID NO: 3):

```
MATLLRSKLSNVATSVSNKSQAKMSGMFARMGFQAATDE
EAVGFAHCDDLDFEHRQGLQMDILKAEGEPCGDEGAEAP
VEGDIHYQRGSGAPLPPSGSKDQVGGGGEFGGHDKPKIT
AWEAGWNVTNAIQGMFVLGLPYAILHGGYLGLFLIIFAA
VVCCYTGKILIACLYEENEDGEVVRVRDSYVAIANACCA
PRFPTLGGRVVNVAQIIELVMTCILYVVVSGNLMYNSFP
GLPVSQKSWSIIATAVLLPCAFLKNLKAVSKFSLLCTLA
HFVINILVIAYCLSRARDWAWEKVKFYIDVKKFPISIGI
IVFSYTSQIFLPSLEGNMQQPSEFHCMMNWTHIAACVLK
GLFALVAYLTWADETKEVITDNLPGSIRAVVNIFLVAKA
LLSYPLPFFAAVEVLEKSLFQEGSRAFFPACYSGDGRLK
SWGLTLRCALVVFTLLMAIYVPHFALLMGLTGSLTGAGL
CFLLPSLFHLRLLWRKLLWHQVFFDVAIFVIGGICSVSG
FVHSLEGLIEAYRTNAED.
```

See also, for example, GenBank Accession No.: NM_080552, Homo sapiens solute carrier family 32 member 1 (SLC32A1), mRNA, which provides the nucleic acid sequence (SEQ ID NO: 4):

```
   1 gctcgcgccc cgcggcagct ccgcagtgca
     ctagccacca ccgccgccgc cgccgctccg
  61 ccagacctgc tgccagcttg cccggtccag
     ccctgagaga gcctcgaacg ccagctgcga
 121 gggtcatgag ccagagagcc ccggggcgcc
     gcgcggagag caagcggaga tagcgacttt
 181 gcgccccca gccctcgcct tcttgcatcg
     cgttcccgc atcctcgggt ccttctgtcc
 241 tttccgctgt ccccaccgcc gccatggcca
     ccttgctccg cagcaagctg tccaacgtgg
 301 ccacgtccgt gtccaacaag tcccaggcca
     agatgagcgg catgttcgcc aggatgggtt
 361 ttcaggcgg cacggatgag gaggcggtgg
     gcttcgcgca ttgcgacgac ctcgactttg
 421 agcaccgcca gggcctgcag atggacatcc
     tgaaagccga gggagagccc tgcggggacg
 481 agggcgctga agcccccgtc gagggagaca
     tccattatca gcgaggcagc ggagctcctc
 541 tgccgcccctc cggctccaag gaccaggtgg
     gaggtggtgg cgaattcggg ggccacgaca
 601 agcccaaaat cacggcgtgg gaggcaggct
     ggaacgtgac caacgccatc cagggcatgt
 661 tcgtgctggg cctaccctac gccatcctgc
     acggcggcta cctggggttg tttctcatca
 721 tcttcgccgc cgttgtgtgc tgctacaccg
     gcaagatcct catcgcgtgc ctgtacgagg
 781 agaatgaaga cggcgaggtg gtgcgcgtgc
     gggactcgta cgtggccata gccaacgcct
 841 gctgcgcccc gcgcttccca acgctgggcg
     gccgagtggt gaacgtagcg cagatcatcg
 901 agctggtgat gacgtgcatc ctgtacgtgg
     tggtgagtgg caacctcatg tacaacagct
 961 tcccggggct gcccgtgtcg cagaagtcct
     ggtccattat cgccacggcc gtgctgctgc
1021 cttgcgcctt ccttaagaac ctcaaggccg
     tgtccaagtt cagtctgctg tgcactctgg
1081 cccacttcgt catcaatatc ctggtcatag
     cctactgtct atcgcgggcg cgcgactggg
1141 cctggagaa ggtcaagttc tacatcgacg
     tcaagaagtt ccccatctcc attggcatca
```

-continued
```
1201 tcgtgttcag ctacacgtct cagatcttcc
     tgccttcgct ggagggcaat atgcagcagc
1261 ccagcgagtt ccactgcatg atgaactgga
     cgcacatcgc agcctgcgtg ctcaagggcc
1321 tcttcgcgct cgtcgcctac ctcacctggg
     ccgacgagac caaggaggtc atcacggata
1381 acctgcccgg ctccatccgc gccgtggtca
     acatctttct ggtggccaag gcgctgttgt
1441 cctatcctct gccattcttt gccgctgtcg
     aggtgctgga gaagtcgctc ttccaggaag
1501 gcagccgcgc cttttcccg gcctgctaca
     gcggcgacgg gcgcctgaag tcctgggggc
1561 tgacgctgcg ctgcgcgctc gtcgtcttca
     cgctgctcat ggccatttat gtgccgcact
1621 tcgcgctgct catgggcctc accggcagcc
     tcacgggcgc cggcctctgt ttcttgctgc
1681 ccagcctctt tcacctgcgc ctgctctggc
     gcaagctgct gtggcaccaa gtcttcttcg
1741 acgtcgccat cttcgtcatc ggcggcatct
     gcagcgtgtc cggcttcgtg cactccctcg
1801 agggcctcat cgaagcctac cgaaccaacg
     cggaggacta gggcgcaagg gcgagccccc
1861 gccgcgcttc tgcgctctct cccttctccc
     ctcacccgc ccccaccagc ccagtgcgcc
1921 ctgccgccgc gcttgggagg ccaagcttta
     aacatctctg gttcctagtt tctgattatt
1981 cggggatggg gggatggga ggggacaggg
     attcacgatc catcgcgtct gcgtttctgt
2041 tgtcctttct tttccacaac accctggttt
     tgggggagg cggggtgcat ttgcgggcag
2101 ggttctctgt ccttccaagt ggggccccga
     cactttggtt ccagtcatcg aggggggtgg
2161 gaagggaggg agaggggcg cagctcgcag
     gcgtggcaac ttgaccttgg gggaatattt
2221 cacatccatc cagagctcgg aatctacagc
     gtccagccat ttccagcaag agcgcttccc
2281 attccggaga cgtttcaacc ctgcagcggg
     aaaggctgac tgggaaatcc attttgggtg
```

-continued

```
2341 ggcaatttcc ttcaacgaag ccggaaggcg
     agaagccgcg gcggggccag cttgcctgcc
2401 ggttttcagg aatctaaact ctcatcttgt
     gcaatttatc aggtgtggaa ctgttctact
2461 gtgcgtgtgg tgtgctcgtg gtgaataaga
     tgaaatgtat atcagaaaaa aatctatctc
2521 taatttagag tgcggtacat aattatatcc
     gcaaataaag aagagacaaa ggctaaaaaa
2581 a.
```

In addition, nucleic acid sequences for rat VGAT are known in the art. See, for example, GenBank Accession No.: AF030253.1, *Rattus norvegicus* vesicular GABA transporter (VGAT) mRNA, complete cds, which provides the nucleic acid sequence (SEQ ID NO: 6):

```
   1 agcggagata gcggcccttg ctgccttgac
     gcgcgcccgc cgcgtcccca gacccttctg
  61 tccttttctc ccgccccgcc gccgccatgg
     ccaccctgct ccgcagcaag ctgaccaacg
 121 tggccacctc tgtgccaac aagtcccagg
     ccaaggtgag cggcatgttc gccaggatgg
 181 ggtttcaggc ggccacggat gaggaggcgg
     tgggcttcgc gcactgcgac gatctcgact
 241 ttgagcaccg ccagggcctg cagatggaca
     tcctgaaatc ggaaggcgag ccctgcgggg
 301 acgagggcgc agaacctccc gtcgagggag
     acattcatta tcagcgcggc ggcgctcccc
 361 tgccaccctc gggctccaag gaccaggccg
     tgggagctgg tggggagttc gggggtcacg
 421 acaaacccaa gatcacggcg tgggaagcgg
     gctggaacgt gacaaacgcc attcagggca
 481 tgttcgtgct gggtctaccc tacgccatcc
     tccacggcgg ctacctgggg ttgttcctca
 541 tcatcttcgc cgcggtggtg tgctgctaca
     ccggcaagat cctcatcgcg tgcctgtacg
 601 aggagaacga agatggtgag gtggtgcgcg
     tgagggactc gtatgtggcc atagctaacg
 661 cgtgctgcgc tcctcgattc cccacgctgg
     gcggccgcgt ggtcaatgtg gcccagatca
 721 tcgagctggt gatgacgtgt atcttgtacg
     tagtggtgag cggcaacctc atgtacaaca
```

```
 781 gtttcccggg gctgcccgtg tcgcagaagt
     cctggtccat catagccacg gcggtgctgc
 841 tgccctgcgc cttcctgaag aatctcaagg
     ccgtgtccaa gttcagtctg ctgtgcacgc
 901 tggcccactt cgtcatcaac atcctggtca
     tcgcctactg tctctcgcgc gcgcgtgact
 961 gggcctggga gaaggtgaag ttctacatcg
     acgtcaagaa gtttcctatc tccatcggca
1021 tcatcgtgtt cagctacacg tcgcagatct
     tcctgccctc gctcgaaggc aacatgcagc
1081 agccccagcga attccactgc atgatgaact
     ggacacacat cgccgcctgc gtgctcaagg
1141 gtctcttcgc gctcgtcgcc tacctcacct
     gggccgacga gaccaaggaa gtcatcacgg
1201 ataacctgcc cggttccatc cgcgccgtgg
     tcaacatctt cctggtggcc aaggcgctgc
1261 tgtcctaccc gttgcccttc ttcgcggccg
     tcgaagtgct ggagaagtct ctcttccagg
1321 aaggcagtcg tgccttcttc cccgcctgct
     acggtggcga cggtcgcctt aagtcctggg
1381 ggctgacgct gcgctgcgcg ctggtggtct
     tcacgctgct catggccatc tacgtgccac
1441 acttcgcgct gctcatgggc ctcacgggca
     gcctcacggg agccggcctc tgcttcctgc
1501 tgcccagcct cttccacttg cgtcttctct
     ggcgcaagct gctgtggcac caggtcttct
1561 tcgatgtggc catcttcgtc atcggcggca
     tctgcagcgt gtccggcttc gtgcattcac
1621 tcgagggcct catcgaggcc taccgaacca
     acgcagagga ctaggggggcg gggaccctgc
1681 ccccagctcc ctccccgccc accccactc
     ccccttatcc ccgcccccaa cccccacccc
1741 cagcccctg cgcaaccacg ctggggaggc
     cgagctttaa acacctccgg ttcctagttg
1801 ctgattattc ggggaccggg cggggaggg
     aggggatag acatccaagg tccactgcgt
1861 ctgcgtttct gtcgttcttt ctattccaca
     tcgtcctgat ttggggggag ggagcagagc
```

```
             -continued
1921  gtataagtga  agggtatttt  ctgtccttcc tagaacaccc  accaccacca  ccaccaaact 1981  ttggctccag  tcaatgttag  gggtgggaag ggaggggaa   agggaacacg  cagttcgcag 2041  gctcggaaac  ttgaccttgg  gggtggggtg ggggacattt  cacagccatt  cagtgcttgg 2101  aatctactgc  gtccagccat  ttccagcaag agcgctcccc  atgccctaga  catttcaacc 2161  ttgaggcctg  aaaggctgac  cgggaaatcc atttcgggca  ggcgacttcc  ctctggagaa 2221  gccgcggcag  gggcccccgt  ttgcctgccg gttttcagga  acccaaactc  atcttgtgca 2281  atgtatccgg  ttgtggaact  gtatactgtg cgtgtggtgt  gctcgtggtg  aataagatga 2341  aatgtatatc  agaaaaaatc  tatctctaat ttagagtgcg  gtgcctcgtg  cc.
```

In human patients as well as in animal models of chronic neuropathic pain, the mechanism as well as associated neuropathological changes leading to neuropathic pain states are relatively well defined. These can be represented by the presence of peripheral nerve injury-induced neuroma or partial spinal segmental traumatic or ischemic injury. As such, the segmental level as well the site of the origin of pain-inducing stimuli can be identified. Accordingly, the present invention provides treatment strategies which would selectively target a key population of spinal neurons responsible for the transmission of nociceptive stimuli at relevant spinal segments, yet not affect other neuronal populations (such as α-motoneurons or interneurons in non-targeted neighboring segments). The data provided herein demonstrates that subpial delivery of GAD65 and VGAT genes into L3-L5 spinal segments of a mouse model of neuropathic pain provides a potent and long-lasting anti-nociceptive effect.

Preferential expression of GAD65 gene in infected astrocytes (as opposed to neurons) appears to provide a specific advantage with respect to expected GABA mediated anti-spasticity effect (see, e.g., WO2014/116652 and PCT/US2017/024285, each of which is incorporated herein by reference). As has been shown in vitro, infection of primary astrocytes led to a $Ca^{2+}$ independent increase in extracellular GABA concentration. Accordingly, it is expected that astrocyte-mediated GABA release in the spinal parenchyma will be independent of the functionality and connectivity of local neuronal inhibitory circuitry and will specifically exert its hyperpolarizing effect on $GABA_B$ receptor expressed on Ia afferents and/or α-motoneurons. The biological activity of astrocyte-produced GABA was confirmed by its depolarization-inducing effect on preferentially $GABA_A$ receptor-expressing cultured hNT neurons.

The use of a dual GAD65 and VGAT gene therapy represents a novel approach not previously tested in the context of spinal or brain delivery with the goal to increase regional neuronal inhibition. First, this approach uses subpial administration of a vector delivered in small quantities, which leads to only a localized infection of neurons in the dorsal horn of the vector-injected segment that is unilateral to the site of peripheral nerve injury. This is in contrast to an intrathecal delivery technique where the vector is effective in infecting ventral horn neurons and dorsal root ganglion cells throughout the injected regions (left and right and over multiple segments). No dorsal horn neurons (which are the primary neuronal population responsible for spinal transmission of nociceptive stimuli into brain) are infected after intrathecal delivery of the vector. Second, combination of the GAD65 and VGAT genes is required for effective induction of nociceptive effect by potentiating release of vesicular GABA from infected dorsal horn neurons into synaptic cleft.

Accordingly, in one aspect, the invention provides a method of treating neuropathic pain in a subject by spinal-specific upregulation of the GAD65 gene and VGAT gene. In various embodiments, the method includes subpial administration of a viral vector encoding GAD65 and VGAT, and expressing the GAD65 and VGAT distally, contralaterally, and/or ipsilaterally to the administration site at a therapeutic level of the subject, thereby decreasing neuropathic pain in the subject. In various embodiments, the vector includes a nucleotide sequence encoding GAD65 and VGAT. Also within the scope of the invention is a polypeptide encoded by a nucleotide sequence that has at least 60% homology to GAD65 or a functional fragment thereof (i.e., a polypeptide encoded by nucleotide sequence that has about 70% homology, about 75% homology, about 80% homology, about 85% homology, about 90% homology, about 95% homology, about 99% homology to GAD65 or a fragment thereof). Also within the scope of the invention is a polypeptide encoded by nucleotide sequence that has at least 60% homology to VGAT or a fragment thereof (i.e., a polypeptide encoded by nucleotide sequence that about 70% homology, about 75% homology, about 80% homology, about 85% homology, about 90% homology, about 95% homology, about 99% homology to VGAT or a fragment thereof).

Viral vectors can be particularly useful for introducing a polynucleotide useful in performing a method of the invention into a target cell. Viral vectors have been developed for use in particular host systems, particularly mammalian systems and include, for example, retroviral vectors, other lentivirus vectors such as those based on the human immunodeficiency virus (HIV), adenovirus vectors (AV), adeno-associated virus vectors (AAV), herpes virus vectors, vaccinia virus vectors, and the like (see Miller and Rosman, *BioTechniques* 7:980-990, 1992; Anderson et al., *Nature* 392:25-30 *Suppl.*, 1998; Verma and Somia, *Nature* 389:239-242, 1997; Wilson, *New Engl. J. Med.* 334:1185-1187 (1996), each of which is incorporated herein by reference). In one aspect of the invention, a lentivirus, an AV, or an AAV is utilized.

Adenoviruses represent the largest nonenveloped viruses, because they are the maximum size able to be transported through the endosome (i.e., envelope fusion is not necessary). The virion also has a unique "spike" or fibre associated with each penton base of the capsid that aids in attachment to the host cell. AAV is a dependent parvovirus that by definition requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells.

Once in the nucleus, the virus uncoats and the transgene is expressed from a number of different forms—the most persistent of which are circular monomers. AAV will integrate into the genome of 1-5% of cells that are stably transduced (Nakai et al., *J. Virol.* 76: 11343-349, 2002). Expression of the transgene can be exceptionally stable. Because progeny virus is not produced from AAV infection in the absence of helper virus, the extent of transduction is restricted only to the initial cells that are infected with the virus. It is this feature which makes AAV a suitable gene therapy vector for the present invention.

Additional references describing adenovirus vectors and other viral vectors which could be used in the methods of the present invention include the following: Horwitz, M. S., Adenoviridae and Their Replication, in Fields, B., et al. (eds.) *Virology*, Vol. 2, Raven Press New York, pp. 1679-1721, 1990); Graham, F., et al., pp. 109-128 in *Methods in Molecular Biology*, Vol. 7: Gene Transfer and Expression Protocols, Murray, E. (ed.), Humana Press, Clifton, N.J. (1991); Miller, N., et al., FASEB Journal 9: 190-199, 1995; Schreier, H, *Pharmaceutica Acta Helvetiae* 68: 145-159, 1994; Schneider and French, Circulation 88:1937-1942, 1993; Curiel D. T., et al., *Human Gene Therapy* 3: 147-154, 1992; Graham, F. L., et al., WO 95/00655 (5 Jan. 1995); Falck-Pedersen, E. S., WO 95/16772 (22 Jun. 1995); Denefle, P. et al., WO 95/23867 (8 Sep. 1995); Haddada, H. et al., WO 94/26914 (24 Nov. 1994); Perricaudet, M. et al., WO 95/02697 (26 Jan. 1995); Zhang, W., et al., WO 95/25071 (12 Oct. 1995). A variety of adenovirus plasmids are also available from commercial sources, including, e.g., Microbix Biosystems of Toronto, Ontario (see, e.g., Microbix Product Information Sheet: Plasmids for Adenovirus Vector Construction, 1996).

Additional references describing AAV vectors which could be used in the methods of the present invention include the following: Carter, B., *Handbook of Parvoviruses*, vol. I, pp. 169-228, 1990; Berns, *Virology*, pp. 1743-1764 (Raven Press 1990); Carter, B., *Curr. Opin. Biotechnol.,* 3: 533-539, 1992; Muzyczka, N., *Current Topics in Microbiology and Immunology,* 158: 92-129, 1992; Flotte, T. R., et al., *Am. J. Respir. Cell Mol. Biol.* 7:349-356, 1992; Chatterjee et al., *Ann. NY Acad. Sci.,* 770: 79-90, 1995; Flotte, T. R., et al., WO 95/13365 (18 May 1995); Trempe, J. P., et al., WO 95/13392 (18 May 1995); Kotin, R., *Human Gene Therapy,* 5: 793-801, 1994; Flotte, T. R., et al., *Gene Therapy* 2:357-362, 1995; Allen, J. M., WO 96/17947 (13 Jun. 1996); and Du et al., *Gene Therapy* 3: 254-261, 1996.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, avian AAV, bovine AAV, canine AAV, equine AAV, ovine AAV, and any other AAV now known. AAV vectors are derived from single-stranded (ss) DNA parvoviruses that are nonpathogenic for mammals (reviewed in Muzyscka (1992) Curr. Top. Microb. Immunol., 158:97-129, incorporated herein by reference). Briefly, AAV-based vectors have the rep and cap viral genes that account for 96% of the viral genome removed, leaving the two flanking 145-basepair (bp) inverted terminal repeats (ITRs), which are used to initiate viral DNA replication, packaging and integration. In the absence of helper virus, wild-type AAV integrates into the human host-cell genome with preferential site-specificity at chromosome 19q 13.3 or it may remain expressed episomally. A single AAV particle can accommodate up to 5 kb of ssDNA, therefore leaving about 4.5 kb for a transgene and regulatory elements, which is typically sufficient. However, trans-splicing systems as described, for example, in U.S. Pat. No. 6,544,785, may nearly double this limit. Adeno-associated virus of many serotypes have been extensively studied and characterized as gene therapy vectors. Those skilled in the art will be familiar with the preparation of functional AAV-based gene therapy vectors. Numerous references to various methods of AAV production, purification and preparation for administration to human subjects can be found in the extensive body of published literature (see, e.g., Viral Vectors for Gene Therapy: Methods and Protocols, ed. Machida, Humana Press, 2003, incorporated herein by reference). Additionally, AAV-based gene therapy targeted to cells of the CNS has been described in U.S. Pat. Nos. 6,180,613 and 6,503,888 (each of which are incorporated herein by reference).

Optionally, the AAV viral capsid is AAV2/9, AAV9, AAVrh8, AAVrh10, AAV Anc80, or AAV PHP.B; however, the serotype of the viral capsid used in certain embodiments of the invention can be selected from among known viral capsids, including AAV viral capsids of other known serotypes.

Optionally, the gene therapy vector, e.g., AAV or AAV-based vector, can be modified to improve virus uptake into the target tissue of interest, viral stability, and tropism. For example, the capsid of an AAV vector may be modified with a ligand (e.g., synthetic or naturally occurring small molecule, peptide, or polypeptide, or other biomolecule) that binds to a receptor at or in the tissue of interest. Other modifications are possible to improve and/or enhance the functional properties of the vector being used to both target the tissue of interest and allow the construct to enter and effectively transduce the target cells. Such modifications will be within the skill set of a person having ordinary skill in the art.

Depending on the host cell/vector system utilized, any of a number of suitable transcription and translation elements, including constitutive and inducible promoters, transcription enhancer elements, transcription terminators, and the like can be used in the expression vector (Bitter et al., *Meth. Enzymol.* 153:516-544, 1987). As defined above, reference to a "promoter" or "promoter sequence" is to be taken in its broadest context and includes a DNA regulatory region capable of binding RNA polymerase in a cell and initiating transcription of a polynucleotide or polypeptide coding sequence such as messenger RNA, ribosomal RNAs, small nuclear of nucleolar RNAs or any kind of RNA transcribed by any class of any RNA polymerase. "Promoters" contemplated herein may also include the transcriptional regulatory sequences of a classical genomic gene, including the Goldberg-Hogness box which is required for accurate transcription initiation in eukaryotic cells, with or without a CAT box sequence and additional regulatory elements (i.e., upstream activating sequences, enhancers and silencers).

Placing a sequence under the regulatory control of a promoter sequence means positioning said molecule such that expression is controlled by the promoter sequence. Promoters are generally positioned 5' (upstream) to the genes that they control. In the construction of heterologous promoter/structural gene combinations, generally promoter position may be a distance from the gene transcription start site that is approximately the same as the distance between that promoter and the gene it controls in its natural setting, i.e., the gene from which the promoter is derived. As is known in the art, some variation in this distance can be accommodated without loss of promoter function. Similarly, the positioning of a regulatory sequence element with respect to a heterologous gene to be placed under its control is defined by the positioning of the element in its natural setting, i.e., the genes from which it is derived. Again, as is known in the art, some variation in this distance can also occur.

Promoter sequences having differing characteristics and expression profiles are well known in the art, including those that are tissue-specific, tissue-non-specific, constitutive, and inducible. Reference can be further made to, for example, Papadakis et al., "Promoters and Control Elements: Designing Expression Cassettes for Gene Therapy." Current Gene Therapy, 2004, 4, 89-113, the contents of which are incorporated herein by reference. Promoters contemplated by the present invention include, but are not limited to: Apo A-I, ApoE, serpina (TBG), alpha-1-antitrypsin (hAAT) (liver specific); MCK (muscle specific); GFAP, NSE, Synapsin I, Preproenkephalin, Dopamine b-hydroxylase (dbH), Prolactin, Myelin basic protein (neuronal-specific), GUSB, CBA, CAG, Ankyrin (erythroid specific), human ubiquitin promoter (UBI) and human synapsin promoter. However, other known tissue-specific or cell-specific promoters may be used.

Suitable host cells for producing recombinant AAV particles include, but are not limited to, microorganisms, yeast cells, insect cells, and mammalian cells, that can be, or have been, used as recipients of a exogenous nucleic acid molecule. Thus, a "host cell" as used herein generally refers to a cell which has been transfected with an exogenous nucleic acid molecule. The host cell includes any eukaryotic cell or cell line so long as the cell or cell line is not incompatible with the protein to be expressed, the selection system chosen or the fermentation system employed.

The AAV vectors can be formulated into preparations for injection or administration by dissolving, suspending or emulsifying them in appropriate, pharmaceutically acceptable carriers or diluents. Examples of such pharmaceutically acceptable carriers or diluents include an aqueous or non-aqueous solvent, such as oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

If a viral vector specific for the cell type is not available, the vector can be modified to express a receptor (or ligand) specific for a ligand (or receptor) expressed on the target cell, or can be encapsulated within a liposome, which also can be modified to include such a ligand (or receptor). A peptide agent can be introduced into a cell by various methods, including, for example, by engineering the peptide to contain a protein transduction domain such as the human immunodeficiency virus TAT protein transduction domain, which can facilitate translocation of the peptide into the cell. In addition, there are a variety of biomaterial-based technologies such as nano-cages and pharmacological delivery wafers (such as used in brain cancer chemotherapeutics) which may also be modified to accommodate this technology.

Accordingly, in another aspect, the present invention provides gene therapy vectors or constructs comprising GAD65 and/or VGAT genes, or derivatives and/or mutants thereof, which are operably linked to at least a promoter element that is capable of being expressed in a tissue of the central nervous system. As demonstrated herein using accepted mouse, rat, and pig models, the gene therapy vectors of the present invention were effective in treating neuropathic pain and/or muscle spasticity.

Thus, in various embodiments, the serotype of the viral vector used in the invention may be selected from the group consisting of AAV1, AAV2, AAV3, AAV4, AAV5, AAV6, AAV7, AAV8, AAV9, AAVrh8, AAVrh10, AAVrh33, AAV rh34, AAV Anc80 (Anc80), AAV PHP.B, and others (see, e.g., Cao et al. (2002) PNAS, 99:11854-11859; and Viral Vectors for Gene Therapy: Methods and Protocols, ed. Machida, Humana Press, 2003, incorporated herein by reference). Other serotypes besides those listed herein are also contemplated. In certain exemplary embodiments, AAV9 or Anc80 are used. It is also contemplated that the disclosed compositions and methods may use AAV chimeric vectors, whereby portions of AAV are fused with other similar vectors, such as Adenovirus.

In various embodiments, the gene therapy constructs described herein may also comprise a vector (or gene therapy expression vector) into which the gene(s) of interest (e.g., GAD65 and/or VGAT) is cloned or otherwise which includes the gene(s) of interest in a manner such that the nucleotide sequences of the vector allow for the expression (constitutive or otherwise regulated in some manner) of the gene(s) of interest. The vector constructs herein described include any suitable gene expression vector that is capable of being delivered to a tissue of interest (e.g., CNS) and which will provide for the expression of the gene of interest in the selected tissue of interest (e.g., CNS).

Accordingly, the present invention also provides a gene therapy composition comprising the GAD65 and/or VGAT—providing vector(s) as described herein. The gene therapy composition of the invention may therefore include the vector(s) as described herein and one or more pharmaceutically acceptable carriers for gaining entry into a cell or tissue, e.g., a CNS cell or tissue, for treating neuropathic pain or muscle spasticity. Advantageously, the gene therapy composition of the invention provides for a controlled delivery of an active gene, especially a therapeutic gene, to a site of action at an optimum rate and therapeutic dose. Association of the gene therapy vector and/or viral vector containing such gene therapy vector with a delivery system enables, in particular, its specific delivery to the site of action or its controlled expression of genes after targeting the action site.

In addition to cells integrating gene transfer after the use of lentiviral vectors, there are reports of successful GAD65 gene overexpression after AAV-GAD65 injections into sub-thalamic nuclei. In those studies, persistent GAD65 expression was seen up to 4-5 months after AAV-GAD65 injections. More importantly, recent systematic data demonstrate a high efficiency of AAV-based gene delivery into rat or minipig striatum even after a limited number of AAV injections (1-2 injections). Thus, in another embodiment, the present invention employs an AAV-based, genome-non-integrating GAD65-encoding and VGAT-encoding vector to achieve segment-specific GAD65 and VGAT expression.

As demonstrated herein, by combining spinal delivery (i.e., subpial administration) of GAD65 and VGAT (either by using a single vector encoding both genes, or by using separate vectors encoding each individual gene), a significant and functionally relevant decrease in neuropathic pain was achieved. The potency of spinal inhibition was tested in a well-characterized mouse model of chronic neuropathic pain (see, e.g., Pain 76(1-2): 215-222, 1998, incorporated herein by reference).

Administering the instant combinational therapy can be effected or performed using any of the various methods and delivery systems known to those skilled in the art. As used herein, the term "administration" or "administering" is defined to include an act of providing a compound or pharmaceutical composition of the invention to a subject in performing the methods of the invention. Exemplary routes of administration include, but are not limited to, intravenously, intraarticularly, intracisternally, intraocularly, intraventricularly, intrathecally, subpially, intramuscularly, intraperitoneally, intradermally, intracavitarily, and the like, as well as combinations of any two or more thereof. In certain embodiments, the vector composition may be delivered directly into the spinal parenchyma, intrathecal space of the spine, into the spinal subpial space of the subject, and/or into the peripheral spastic muscle to achieve spinal upregulation of the GAD65 gene and VGAT gene. See, e.g., WO2016/122791, incorporated herein by reference.

Thus, the method provided herein permits spinal subpial gene therapy, such as by use of an AAV, in large animals or in humans. An exemplary delivery system for delivering the vector into the subpial space includes a guiding tube bended at 90° and catheter (e.g., PE-5 or PE-10), which permits precise guidance and placement of the subpial catheter into the dorsal subpial space of targeted spinal cord segments. After placement of the catheter, the vector is infused for a certain amount of time before being removed.

As used herein, the term "PE-10" refers to polyethylene tubing having an inner diameter of approximately 0.010 inches. In certain embodiments, the inner diameter of the PE-10 tubing will be about 0.011 inches. Likewise, the term "PE-5" refers to polyethylene tubing having an inner diameter of approximately 0.005 inches. In certain embodiments, the inner diameter of the PE-5 tubing will be about 0.008 inches.

Accordingly, the claimed method provides subpial delivery (i.e., bypassing the pial membrane), which provides near complete spinal parenchymal vector-mediated gene expression in both white and grey matter of the subject being treated. Currently available non-invasive techniques do not permit a comparable level of spinal parenchymal transgene expression or well controlled segment-specific gene silencing.

Figure 7:
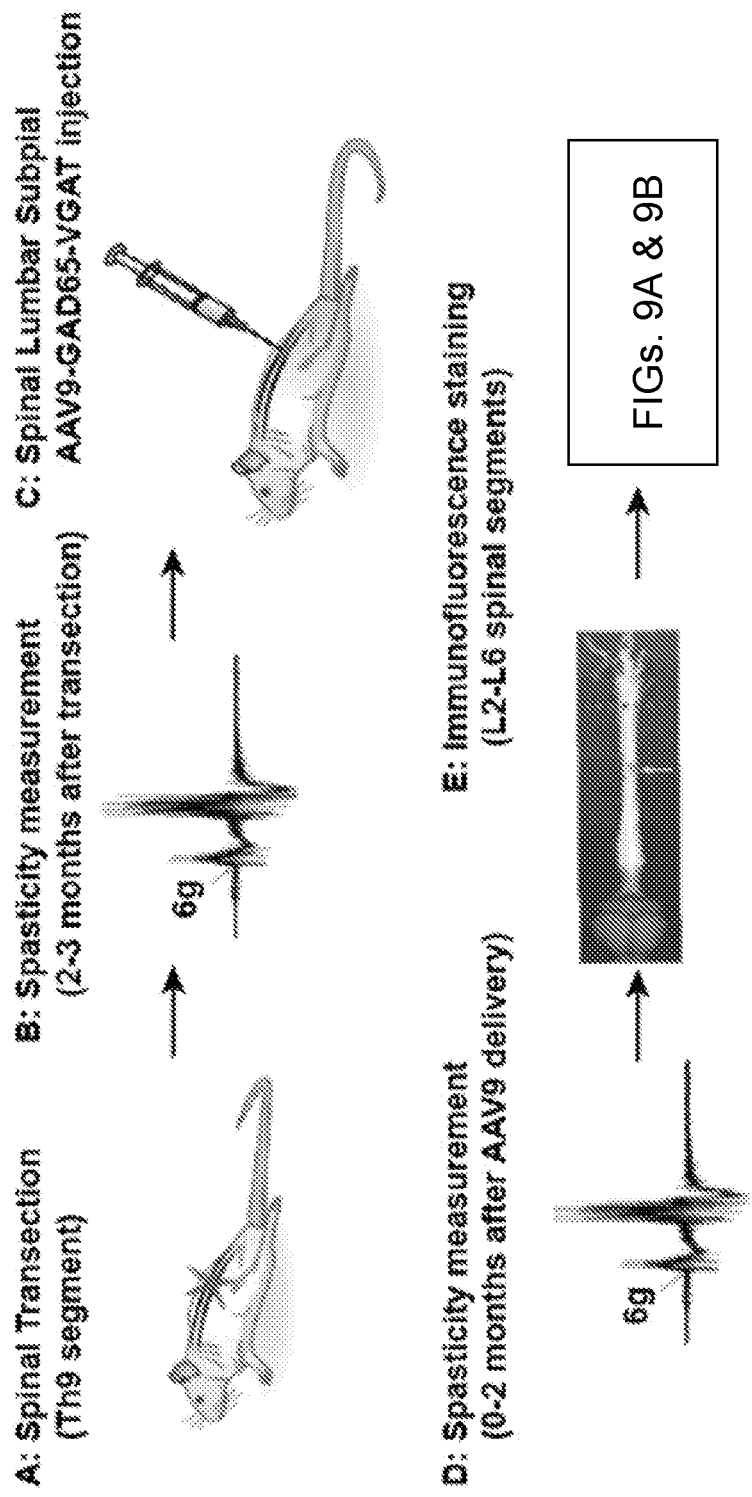
FIG. 7 is a pictorial diagram showing exemplary steps of an experimental design to study the therapeutic anti-spasticity effect of spinal subpial delivery of GAD65 and VGAT genes in a rat model with chronic spinal injury-induced muscle spasticity. Steps A and B show that muscle spasticity in hind limbs is induced by Th9 spinal segment transection and spasticity is identified/measured by quantitative change in gastrocnemius muscle EMG response to paw tactile stimulus. Steps C and D show that 2-3 months after induction of muscle spasticity, the animals received lumbar subpial injection of AAV9 (or Anc80)-UBI-GAD65/VGAT vector and the presence of spasticity response was measured for an additional 2 months. Step E shows that after sacrifice the presence of GAD65 and VGAT upregulation was measured by immunofluorescence staining.

An exemplary method for placing the subpial catheter in a mammalian subject, is shown in FIG. 7, wherein several sequential procedural steps may be followed to minimize potential spinal injury associated with instruments/catheter manipulation in the vicinity of the exposed "dura-free" spinal cord. As shown in steps A and B of FIG. 7, muscle spasticity in hind limbs is induced by Th9 spinal segment transection and spasticity is identified/measured by quantitative change in gastrocnemius muscle EMG response to paw tactile stimulus. 2-3 months after induction of muscle spasticity, the animals received lumbar subpial injection of AAV9 (or Anc80)-UBI-GAD65/VGAT vector and the presence of spasticity response was measured for additional 2 months (FIG. 7; steps C and D). After sacrifice the presence of GAD65 and VGAT upregulation is measured by immunofluorescence staining (FIG. 7; step E).

To deliver a gene therapy vector described herein specifically to a particular region of the central nervous system, especially to the spinal subpial space, it may be administered by stereotaxic microinjection. Thus, in various embodiments, the use of caudal and cranial spinal clamps (placed just above and below the laminectomy) may be used to minimize spinal cord pulsation during catheter placement. Also in various embodiments, an "L" shaped catheter stainless steel guiding tube (e.g., a 16-26 G stainless steel tube bended at 90°) mounted on an XYZ manipulator (as described in, for example, US Pub. No. 2015/0224331, incorporated herein by reference) may be used to facilitate subpial catheter placement.

In certain embodiments, the pia is first punctured using a bent 30G needle. Once the tip of the penetrating needle (e.g., a 30G needle) is in the subpial space for about 1-1.5 mm, the pia may be slightly lifted by 1-2 mm. The subpial catheter is then placed into the subpial space by advancing the catheter from the guiding tube. After the catheter is advanced into the targeted length, the penetrating needle tip of the guiding tube is removed from the subpial space. The vector in a pharmaceutically acceptable carrier may then be injected. Once vector injection is completed (typically over 2-5 min, and in some embodiments, over about 3 min), the catheter is pulled out of the subpial space and the dura is closed. By using this technical approach, placement of the subpial catheter may be accomplished within about 3-5 min from the moment of dura opening. Thereafter, the transgene is expressed distal, contralateral, and/or ipsilateral to the administration site at a therapeutic level.

The term "therapeutically effective amount" or "effective amount" means the amount of the compound or composition that will elicit the biological or medical response of a tissue, system, animal or human that is being sought by the researcher, veterinarian, medical doctor or other clinician, e.g., spinal upregulation of the GAD65 gene and VGAT gene. Thus, the term "therapeutically effective amount" is used herein to denote any amount of a formulation that causes a substantial improvement in a disease condition when applied to the affected areas repeatedly over a period of time. The amount will vary with the condition being treated, the stage of advancement of the condition, and the type and concentration of formulation applied. Appropriate amounts in any given instance will be readily apparent to those skilled in the art or capable of determination by routine experimentation. For example, a "therapeutically effective amount" of, e.g., a vector encoding the GAD65 gene alone or in combination with the VGAT gene or a composition comprising a vector encoding the GAD65 gene and VGAT gene, with respect to the subject method of treatment, refers to an amount of the vector in a preparation which, when applied as part of a desired treatment regimen brings about upregulation of the GAD65 gene and VGAT gene. In some cases, multiple doses of the vector are administered. For example, in some embodiments, in addition to the first administration site, a composition comprising a gene therapy vector described herein carrying a transgene is administered to another site that can be contralateral or ipsilateral to the first administration site.

An effective amount may also depend on the particular vector used. For example, dosages for targeting a CNS tissue may depend on the serotype (e.g., the capsid protein) of the AAV. For example, the AAV may have a capsid protein of an AAV serotype selected from the group consisting of: AAV1, AAV2, AAV5, AAV6, AAV6.2, AAV7, AAV8, AAV9, rh.10, rh.39, rh.43 and CSp3. In certain embodiments, the effective amount of AAV is $10^{10}$, $10^{11}$, $10^{12}$, $10^{13}$, or $10^{14}$ genome copies per kg. In certain embodiments, the effective amount of AAV is $10^{10}$, $10^{11}$, $10^{12}$, $10^{13}$, $10^{14}$, or $10^{15}$ genome copies per subject. In experimental mice, the total volume of injected vector, e.g., AAV vector, solution is, for example, between 0.25 µl and 1.0 µl; whereas the total volume of injected vector solution in experimental pigs is between 50 µl and 150 µl.

Determining a therapeutically or prophylactically effective amount of the delivery vector can be done based on animal data using routine computational methods. Appropriate doses will depend, among other factors, on the specifics of the transfer vector chosen, on the route of administration, on the mammal being treated (e.g., human or non-human primate or other mammal), age, weight, and general condition of the subject to be treated, the severity of the disorder being treated, the location of the area within the heart being treated and the mode of administration. Thus, the appropriate dosage may vary from patient to patient. An appropriate effective amount can be readily determined by one of skill in the art.

Human dosage amounts can initially be determined by extrapolating from the amount of compound used in mice, rats and/or pigs, as a skilled artisan recognizes it is routine in the art to modify the dosage for humans compared to animal models. In certain embodiments it is envisioned that the dosage may vary from between about 1 mg compound/Kg body weight to about 5000 mg compound/Kg body weight; or from about 5 mg/Kg body weight to about 4000 mg/Kg body weight or from about 10 mg/Kg body weight to about 3000 mg/Kg body weight; or from about 50 mg/Kg body weight to about 2000 mg/Kg body weight; or from about 100 mg/Kg body weight to about 1000 mg/Kg body weight; or from about 150 mg/Kg body weight to about 500 mg/Kg body weight. In other embodiments this dose may be about 1, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, 5000 mg/Kg body weight. In other embodiments, it is envisaged that higher doses may be used, such doses may be in the range of about 5 mg compound/Kg body to about 20 mg compound/Kg body. In other embodiments the doses may be about 8, 10, 12, 14, 16 or 18 mg/Kg body weight. Of course, this dosage amount may be adjusted upward or downward, as is routinely done in such treatment protocols, depending on the results of the initial clinical trials and the needs of a particular patient. In certain embodiments, the dosage may be in terms of vector concentration. For example, the concentration of gene therapy vector described herein may be at least: 0.5, 0.75, 1.0, 1.1, 1.2, 1.3, 1.4, 1.5, 1.6, 1.7, 1.8, 1.9 or $2.0 \times 10^{13}$ gc/ml.

Dosage treatment may be a single dose schedule or a multiple dose schedule. Moreover, the subject may be administered as many doses as appropriate. One of skill in the art can readily determine an appropriate number of doses. However, the dosage may need to be adjusted to take into consideration an alternative route of administration, or balance the therapeutic benefit against any side effects. Such dosages may vary depending upon the therapeutic application for which the recombinant vector is employed.

Optionally, AAV-mediated delivery according to the invention may be combined with delivery by other viral and non-viral vectors. Such other viral vectors including, without limitation, adenoviral vectors, retroviral vectors, lentiviral vectors, herpes simplex virus (HSV) vectors, baculovirus vectors, and synthetic vectors may be readily selected and generated according to methods known in the art. Similarly, non-viral vectors, including, without limitation, liposomes, lipid-based vectors, polyplex vectors, molecular conjugates, polyamines and polycation vectors, may be readily selected and generated according to methods known in the art. When administered by these alternative routes, the dosage is desirable in the range described above.

The gene therapy compositions of the invention can be included in a kit and/or pharmaceutical package, container, pack, or dispenser together with instructions for administration. Thus, the present disclosure provides kits for the treatment neuropathic pain and/or muscle spasticity. In one embodiment, the kit includes a therapeutic composition containing an effective amount of gene therapy vector in unit dosage form. In some embodiments, the kit comprises a sterile container which contains a therapeutic composition; such containers can be boxes, ampoules, bottles, vials, tubes, bags, pouches, blister-packs, or other suitable container forms known in the art. Such containers can be made of plastic, glass, laminated paper, metal foil, or other materials suitable for holding medicaments. The instructions will generally include information about the use of the composition for the treatment of neuropathic pain and/or muscle spasticity. In other embodiments, the instructions include at least one of the following: description of the composition; dosage schedule and administration for treatment neuropathic pain and/or muscle spasticity or symptoms associated therewith; precautions; warnings; indications; counter-indications; overdosage information; adverse reactions; animal pharmacology; clinical studies; and/or references. The instructions may be printed directly on the container (when present), or as a label applied to the container, or as a separate sheet, pamphlet, card, or folder supplied in or with the container.

In another aspect, the method of treating neuropathic pain may include a combined therapy wherein local segmental upregulation of the one or more genes described herein is performed in combination with systemic treatment with a GABA uptake inhibitor, such as tiagabine, thereby potentiating the anti-nociceptive effect to only be present in GAD65/VGAT-overexpressing spinal segments and associated dermatomes. Thus, the treatment regimen may include administering a viral vector encoding the GAD65 gene and the VGAT gene in combination with systemic administration of with a GABA uptake inhibitor.

In addition, the methods of the invention can be used in the treatment of nerve damage, such as peripheral neuropathy, which is caused by exposure to toxic compounds, including heavy metals (e.g., lead, arsenic, and mercury) and industrial solvents, as well as drugs including chemotherapeutic agents (e.g., vincristine and cisplatin), dapsone, HIV medications (e.g., Zidovudine, Didanosine, Stavudine, Zalcitabine, Ritonavir, and Amprenavir), cholesterol lowering drugs (e.g., Lovastatin, Indapamid, and Gemfibrozil), heart or blood pressure medications (e.g., Amiodarone, Hydralazine, Perhexiline), and Metronidazole.

The methods of the invention can also be used to treat injury to the nervous system caused by physical, mechanical, or chemical trauma. Thus, the methods can be used in the treatment of peripheral nerve damage caused by physical injury (associated with, e.g., burns, wounds, surgery, and accidents), ischemia, prolonged exposure to cold temperature (e.g., frost-bite), as well as damage to the central nervous system due to, e.g., stroke or intracranial hemorrhage (such as cerebral hemorrhage). Likewise, the methods of the invention can be used in the treatment of chronic pain/nociception caused by such trauma.

The following examples are intended to illustrate but not limit the invention.

Example 1

Vector Delivery in Mouse Model

Figure 1B:
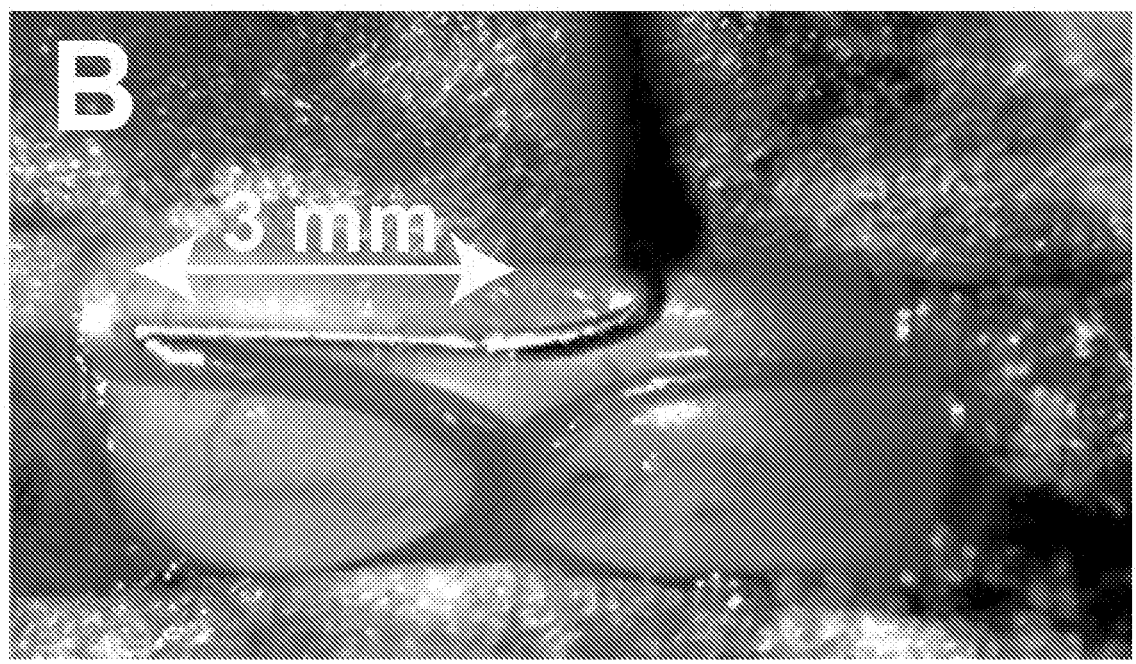

FIGS. 1A and 1B show exemplary subpial delivery of an AAV9 (or Anc80) vector encoding GAD65 (glutamate-decarboxylase 65) and VGAT (vesicular GABA transporter) into targeted segments. Naïve C57BL6 mice had a tight ligature placed around ⅓ to ½ of the diameter of the sciatic nerve (unilateral ligation) to induce mechanical allodynia. After nerve injury animals were tested for changes in tactile nociceptive threshold using von Frey filaments and brush-evoked allodynia for 10 days.

Figure 1C:
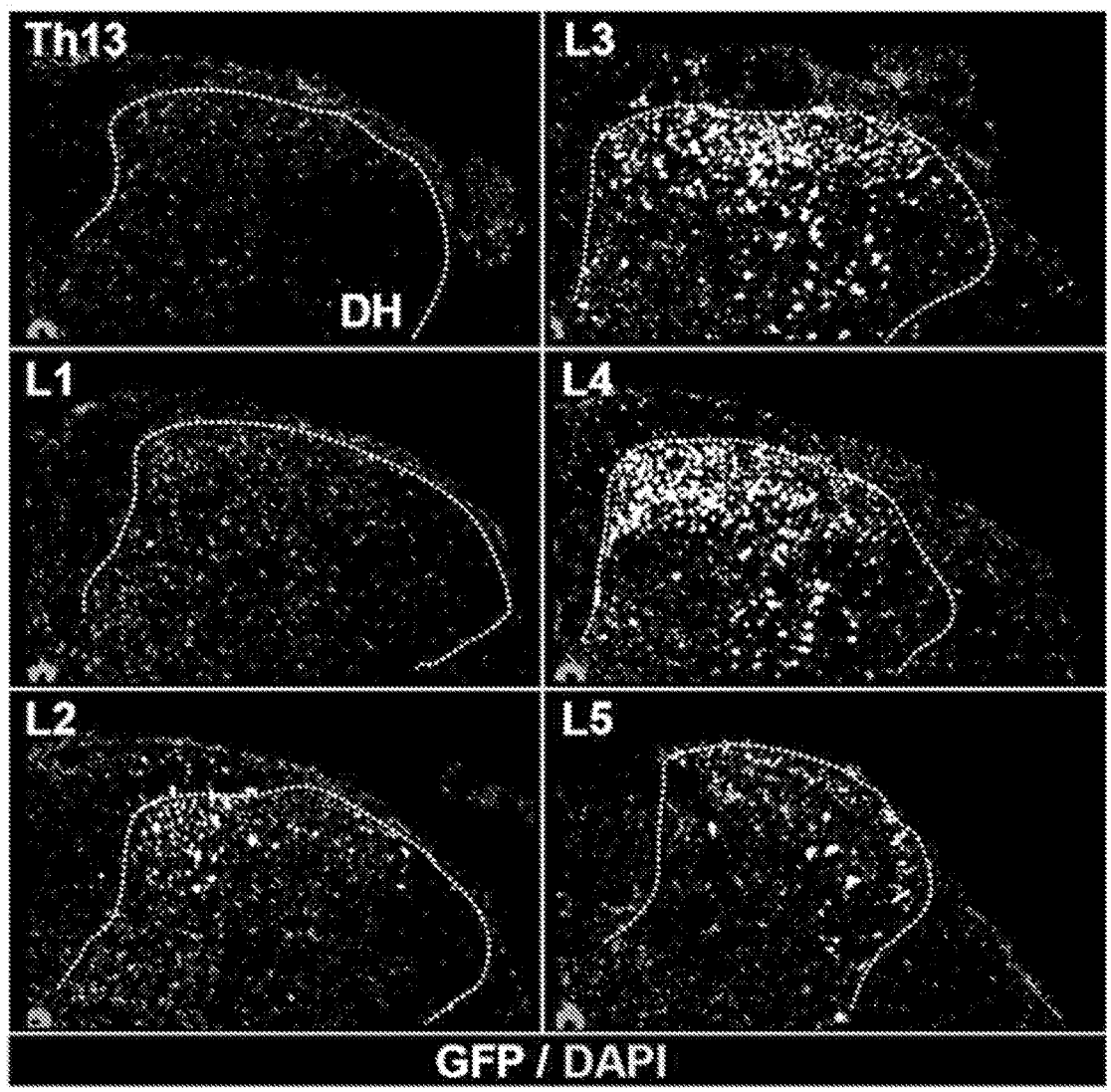

At 10 days after induction of sciatic nerve injury animals received a unilateral subpial injection of AAV9 encoding GAD65 and VGAT gene under ubiquitin promoter (UBI). Two control groups were studied. In the first control group only PBS was injected subpially at L2-L3 in sciatic-nerve-injured animals. In another control group (naïve non-injured animals), no treatment was performed. In a separate group of naïve animals (n=6) using AAV9 encoding GFP, it has been demonstrated that subpial unilateral injection of 0.5 µl of AAV9 ($1.2 \times 10^{13}$ gc/ml; injected into L2-L3 subpial space) selectively infect unilateral dorsal horn neurons in adult mice (FIG. 1C). Thus, the data provided herein demonstrate that use of a subpial vector delivery technique achieves targeted transgene expression that is restricted to dorsal horn neurons and is ipsilateral to vector delivery.

Figure 2A:
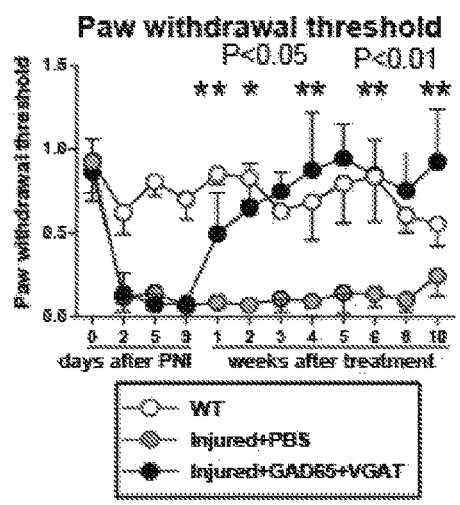
FIGS. 2A-2F are pictorial and graphical diagrams showing anti-nociceptive results after subpial delivery of AAV9-UBI-GAD65/VGAT or Anc80-UBI-GAD65/VGAT in mice with developed neuropathic pain.
Figure 2B:
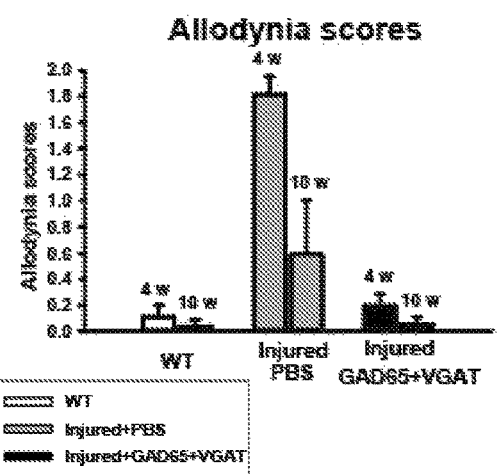

A consistently high degree of tactile hypersensitivity ipsilateral to the site of sciatic nerve ligation was measured in sciatic nerve-injured animals from day 2 after sciatic nerve ligation when the tactile withdrawal threshold decreased from around 1 g (pre-injury baseline) to about 0.2 g. No changes in tactile hypersensitivity were seen in control PBS-injected sciatic nerve-injured animals and all animals showed continuing signs of neuropathic pain (i.e., tactile and brush-evoked hypersensitivity) for up to 10 weeks after subpial PBS delivery (FIGS. 2A and 2B). In contrast, in animals receiving subpial delivery of AAV9-UBI-GAD65/VGAT or Anc80-UBI-GAD65/VGAT, a progressive and complete ($P<0.05$) reversal of tactile and brush-evoked hypersensitivity was seen and persisted for 10 weeks (i.e., the duration of study) (FIGS. 2A, 2B, 2E and 2F). These data demonstrate that unilateral spinal delivery of AAV9-UBI-GAD65/VGAT is highly potent in providing a long-lasting anti-nociceptive effect. Importantly no detectable side effect, such as motor weakness (which is major problem after using systemically or intrathecally delivered anti-nociceptive drugs) was seen.

Figure 2C:
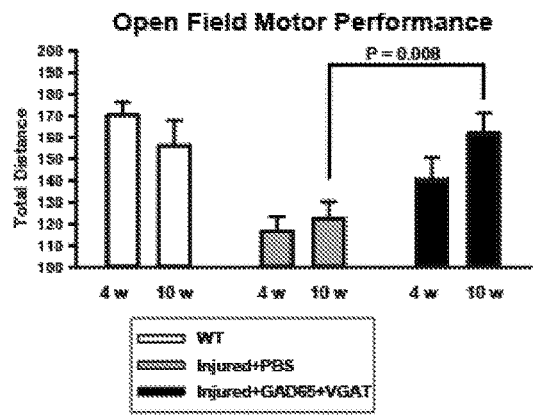
Figure 2D:
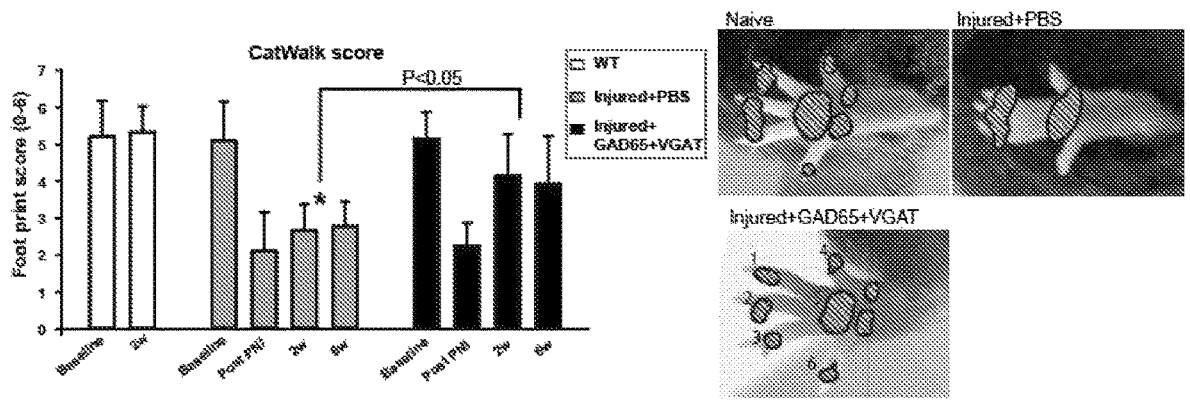
Figure 2E:
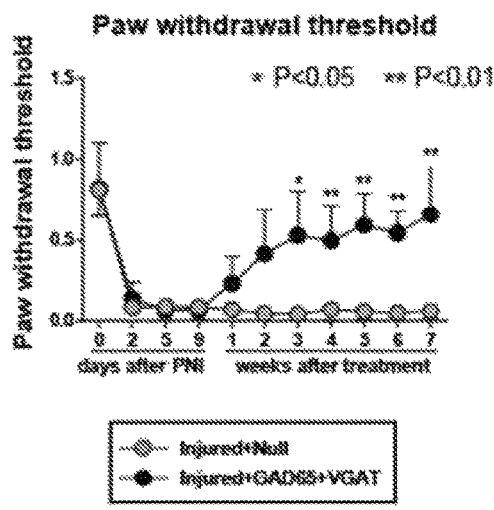
Figure 2F:
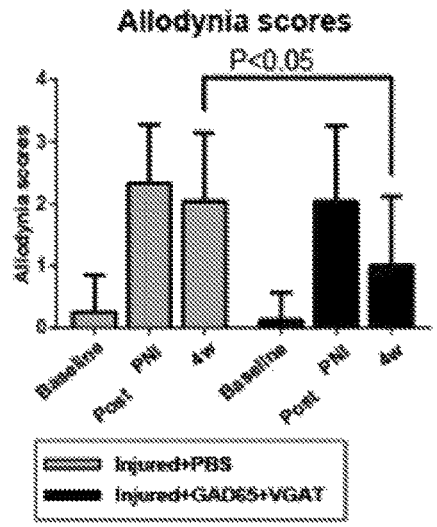
Figure 3A:
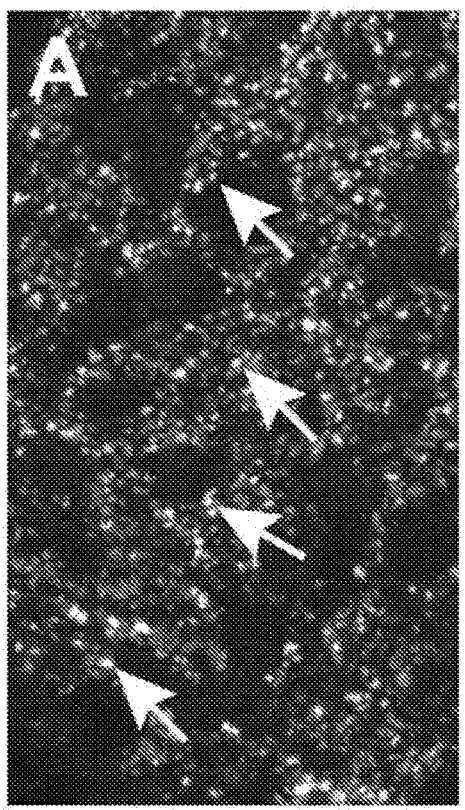
FIGS. 3A-3E are pictorial and graphical diagrams showing induction of mixed inhibitory-excitatory neurotransmitter phenotype in ipsilateral dorsal horn excitatory interneurons after unilateral (ipsilateral) (L2-L4) subpial AAV9-UBI-GAD65/VGAT delivery in adult mice.
Figure 3B:
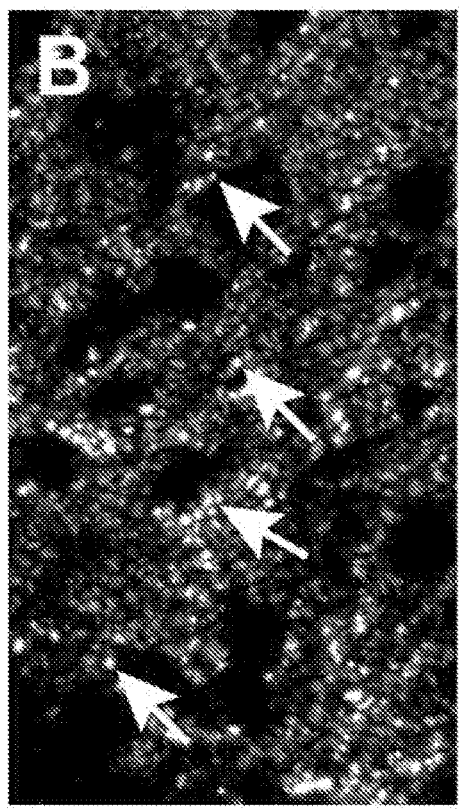
Figure 3C:
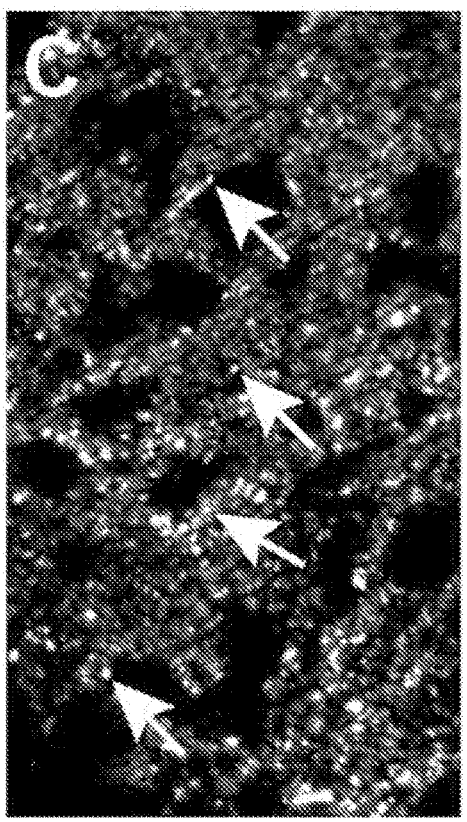
Figure 3D:
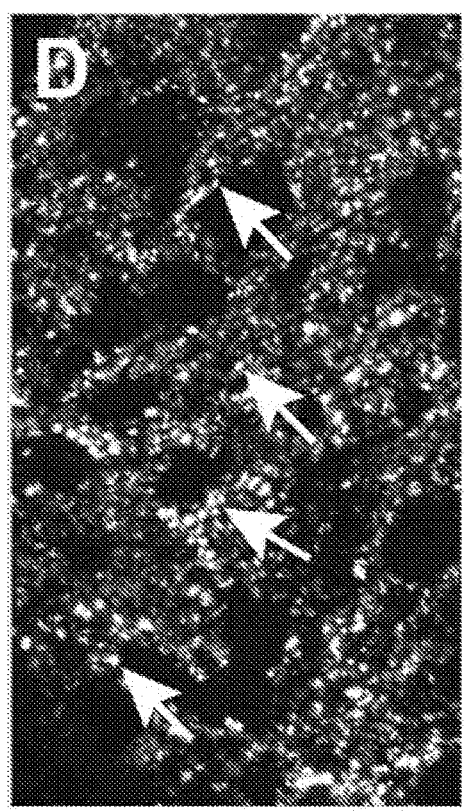
Figure 3E:
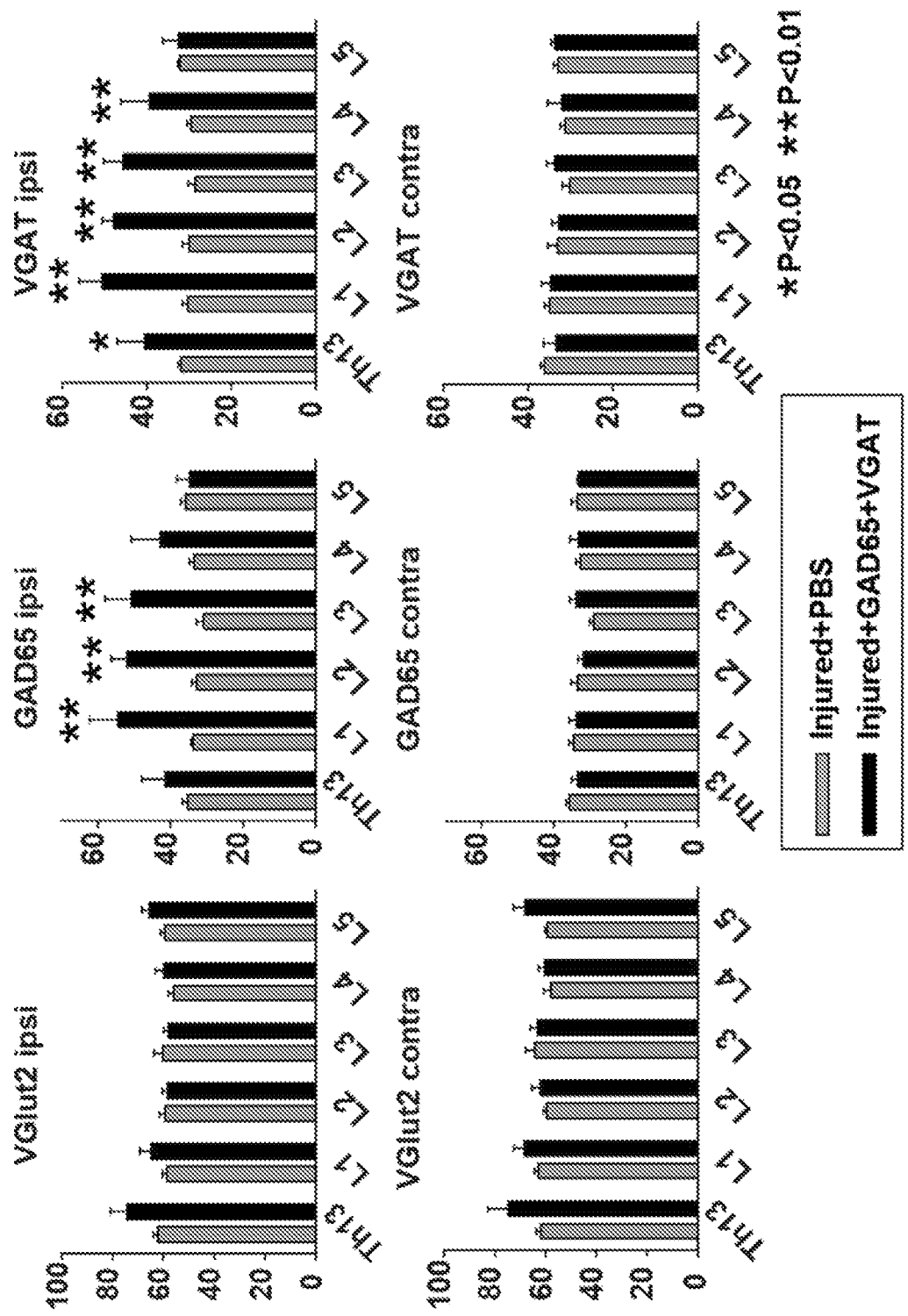

Analysis of open field motor performance (running distance) and ipsilateral hind paw placement pattern (Cat Walk assay) showed a significant increase in running distance and normalization of ipsilateral paw placement in animals treated subpially with AAV9-UBI-GAD65/VGAT (FIGS. 2C and 2D).

As shown in FIGS. 3A-3E, unilateral (ipsilateral) (L2-L4) subpial AAV9-UBI-GAD65/VGAT delivery in adult mice results in induction of mixed inhibitory-excitatory neurotransmitter phenotype in ipsilateral dorsal horn excitatory interneurons. However, staining of contralateral dorsal horn neurons with VGLUT2, GAD65 and VGAT antibodies resulted in detection of no co-localization of VGLUT2 with GAD65 or VGAT. Whereas staining of ipsilateral dorsal horn neurons with the same antibodies demonstrated a clear co-expression of VGLUT2 with VGAT and VGLUT with both GAD65 (FIGS. 3A-3D; white arrows). Likewise, quantitative densitometry analysis showed a significant increase in GAD65 and VGAT expression in ipsilateral dorsal horn (FIG. 3E) injected with AAV9-UBI-GAD65/VGAT vector. No increased expression in contralateral dorsal horn was measured.

Figure 4A:
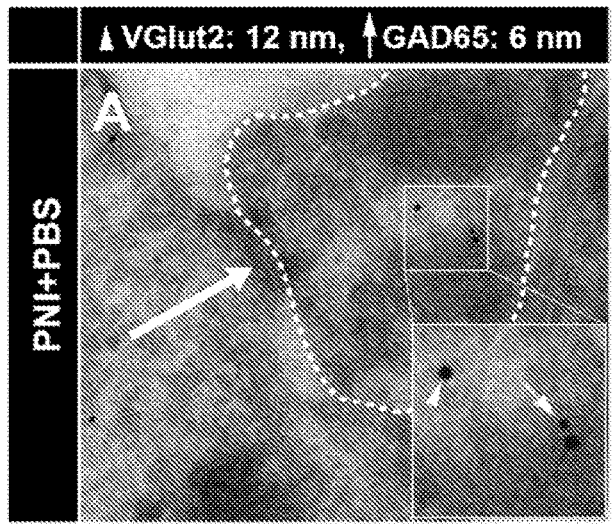
FIGS. 4A-4D are pictorial diagrams showing the results of pre-embedding immune-gold staining with VGLUT2 and GAD65 and VGAT antibodies coupled with electron microscopy that show a clear increase in GAD65 and VGAT immunogold-tagged particles in VGLUT2+ terminals in AAV9-UBI-GAD65/VGAT-injected animals (PNI+GAD65+VGAT) if compared to PBS-injected animals (PNI-PBS).
Figure 4B:
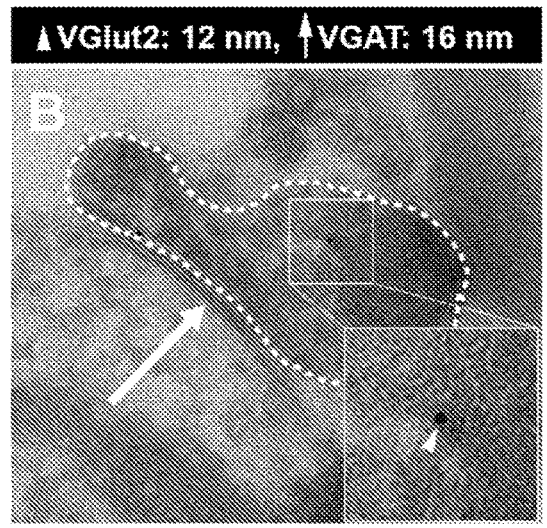
Figure 4C:
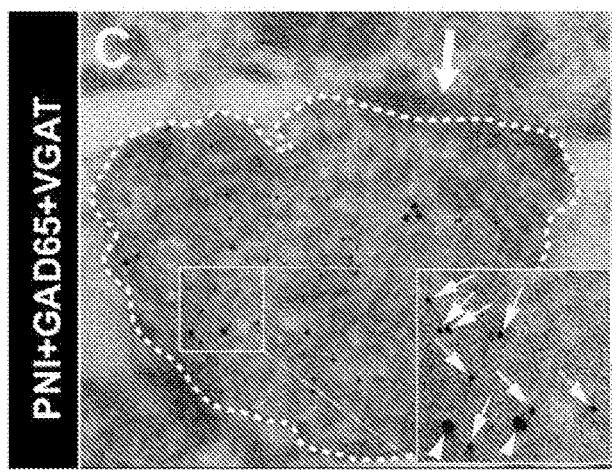
Figure 4D:
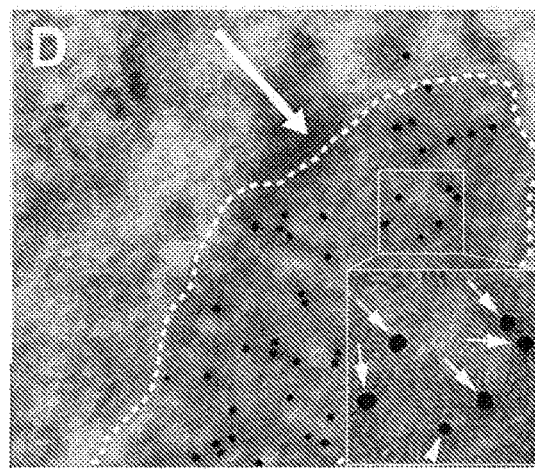
Figure 5A:
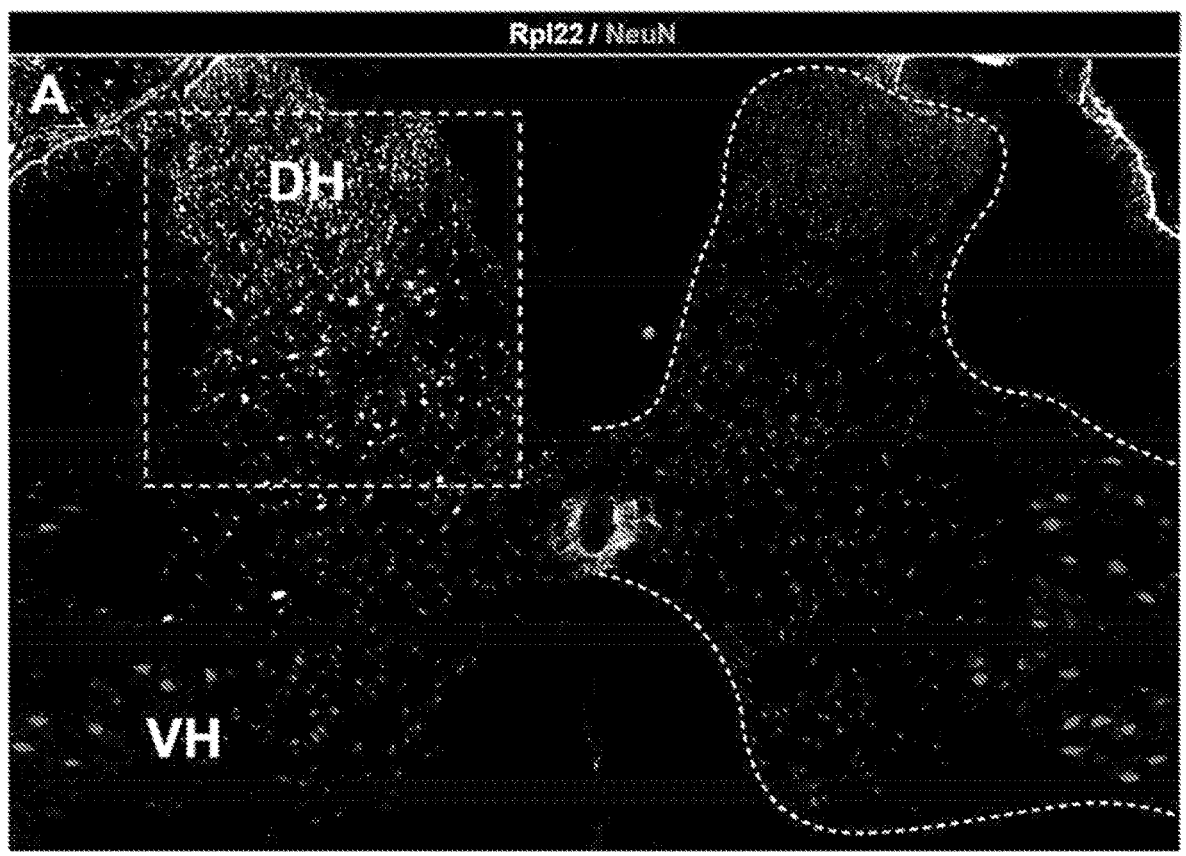
FIGS. 5A-5D are pictorial diagrams showing unilateral Anc80-UBI-Rpl22 (3×HA) delivery in an adult pig model. As shown, ipsilateral dorsal horn neuron-specific Rpl22 protein expression was observed after unilateral subpial (L2-L3) Anc80-UBI-Rpl22-3×HA vector delivery (100 µl; $1.2 \times 10^{13}$ gc/ml) in adult pig model (DH-dorsal horn; VH-ventral horn).
Figure 5B:
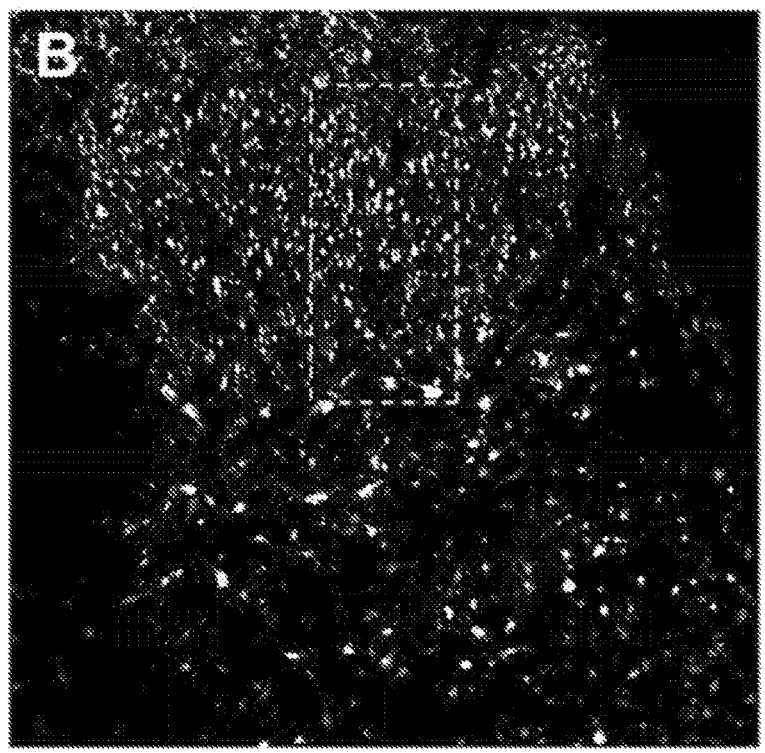
Figure 5C:
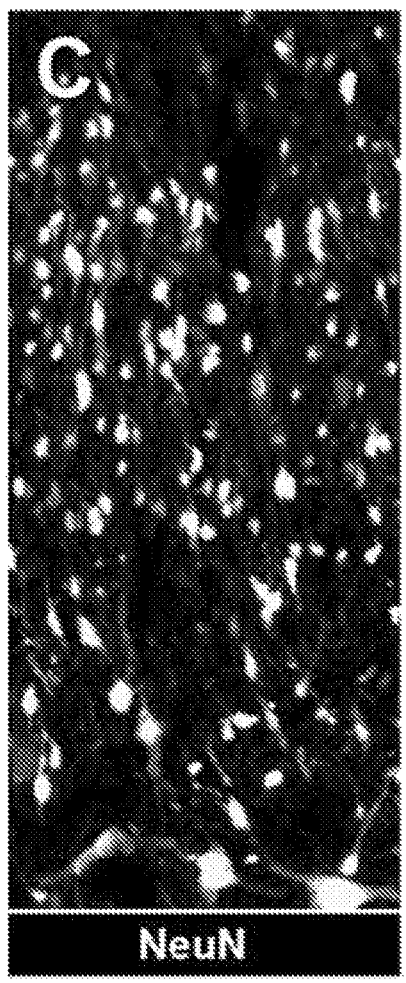
Figure 5D:
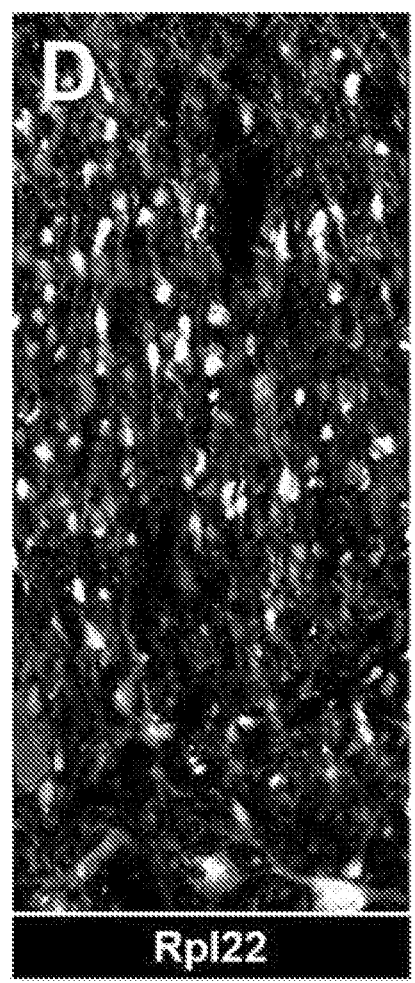
Figure 6A:
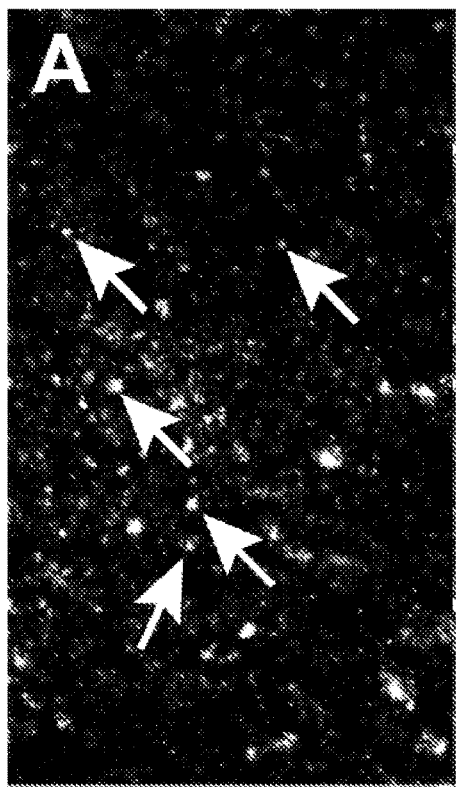
FIGS. 6A-6D are pictorial diagrams showing that unilateral Anc80-UBI-GAD65/VGAT delivery in an adult pig induces mixed excitatory-inhibitory neuronal phenotype in dorsal horn neurons. Staining of ipsilateral dorsal horn neurons with VGLUT2 (FIG. 6A), VGAT (FIG. 6B), and GAD65 (FIG. 6C) antibodies in the animal model (adult pig; 35 kg) injected ipsilaterally with Anc80-UBI-GAD65/VGAT vector (100 µl; $1.2 \times 10^{13}$ gc/ml). As shown, a clear co-expression of VGLUT2 with VGAT and GAD65 (white puncta) can be detected (FIG. 6D).
Figure 6B:
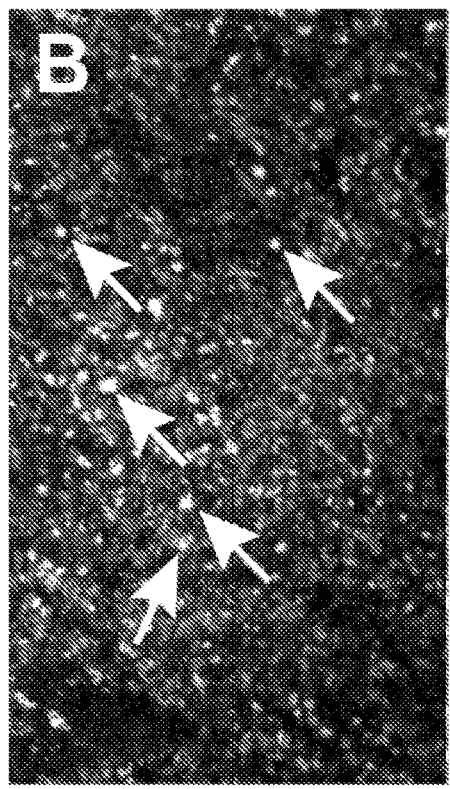
Figure 6C:
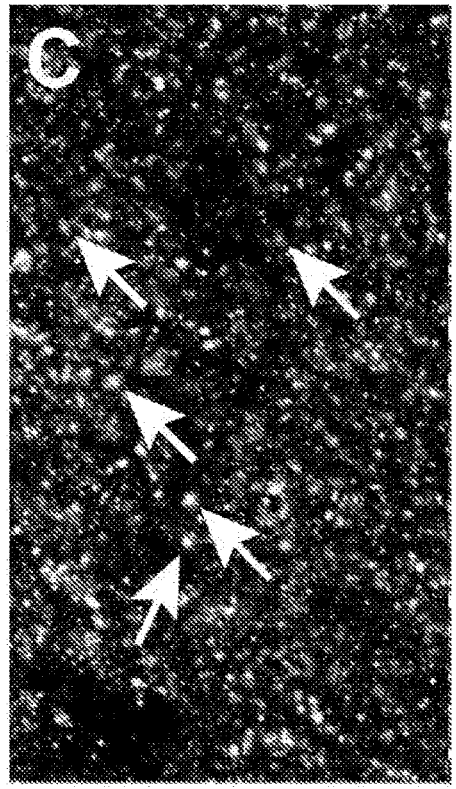
Figure 6D:
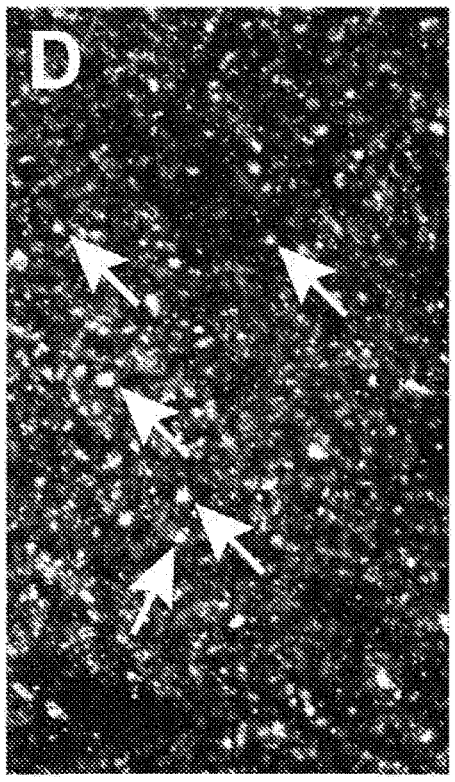

Pre-embedding immune-gold staining with VGLUT2, GAD65 and VGAT antibodies coupled with electron microscopy showed a clear increase in GAD65 and VGAT immunogold-tagged particles in VGLUT2+ terminals in AAV9-UBI-GAD65/VGAT-injected animals (FIGS. 4C and 4D; PNI+GAD65+VGAT:Ipsi images). Minimal or no co-expression of VGLUT2 with GAD65 and VGAT particles was seen in control PBS-injected animals (FIGS. 4A and 4B; PNI+PBS: Ipsi images). Fluorescence in situ hybridization showed a clear appearance of double and triple-tagged neurons with VGLUT2, GAD65 and VGAT mRNA in AAV9-UBI-GAD65/VGAT-injected animals (PNI: GAD65+VGAT; Ipsi images) (FIGS. 4E-4J).

Thus, co-expression of inhibitory neurotransmitter machinery (i.e., GAD65 and VGAT) in excitatory (VGLUT2) neurons/terminals leads to a measured anti-nociceptive effect with improved motor performance in animal models. Further, the induction of a dual excitatory-inhibitory neurotransmitter phenotype leads to a preferential inhibitory effect after activation of peripheral nociceptive afferents.

Example 2

Vector Delivery in Pig Model

In this example, an adult pig model was used to demonstrate that subpial delivery of a vector achieves a well targeted transgene expression in an animal species that has similar spinal cord dimension to that of an adult human. Adult pigs (Yucatan pigs, 15-25 kg; n=3) received unilateral subpial (L2-L3) Anc80-UBI-Rpl22-3xHA vector delivery (100 µl; $1.2 \times 10^{13}$ gc/ml). After vector injections, animals survived for 48 hrs and were then perfusion-fixed with 4% paraformaldehyde. Transverse spinal cord sections were then prepared and stained with anti-HA antibody. Stained sections were analyzed with confocal microscopy. As shown in FIGS. 5A-5D, dorsal horn neuron-specific Rpl22 protein expression ipsilateral to the side of vector injection was observed.

A different group of adult pigs (Gottingen-Minnesota; 35-45 kg; n=3) received unilateral subpial (L2-L3) Anc80-UBI-GAD65/VGAT (100 µl; $1.2 \times 10^{13}$ gc/ml) to demonstrate induction of mixed excitatory-inhibitory neuronal phenotype in infected neurons, similar to what was observed in the mouse model. After vector injections, the animals survived for 8 weeks and were periodically assessed for open field motor performance. No detectable motor weakness was observed in any animal. At 8 weeks animals were perfusion-fixed with 4% paraformaldehyde and transverse spinal cord sections prepared from L1-L4 segments. Sections were stained with anti-VGLUT2, GAD65 and VGAT antibody and analyzed with confocal microscopy.

As shown in FIGS. 6A-6D, staining of ipsilateral dorsal horn neurons with VGLUT2, GAD65 and VGAT antibodies showed clear co-expression of VGLUT2 with VGAT and GAD65. Thus, by manipulating the volume of vector delivered into subpial space a comparable multisegmental expression of targeted transgene can be achieved in a spinal cord that has similar dimensions to that of an adult human spinal cord.

Example 3

Vector Delivery in Rat Model of Chronic Muscle Spasticity

In a rat model for chronic muscle spasticity (i.e., rats with spinal transection-induced muscle spasticity), vector therapy was provided to demonstrate anti-spasticity effect after subpial delivery of AAV9-UBI-GAD65/VGAT. As shown in FIGS. 8A and 8B, measurement of muscle spasticity in animals receiving a control vector (AAV9-GFP) showed progressive increase in muscle spasticity for 8 weeks after virus delivery (compared to baseline measured at 2-3 months after spinal transection). In contrast a near complete block of spasticity response was measured in animals receiving AAV9-UBI-GAD65/VGAT vector. Measurement of rate-dependent depression (RDD) of H-reflex showed a significant recovery of RDD in animals treated with AAV9-UBI-GAD65/VGAT vector (FIGS. 8C and 8D).

Figures 9A, 9B:
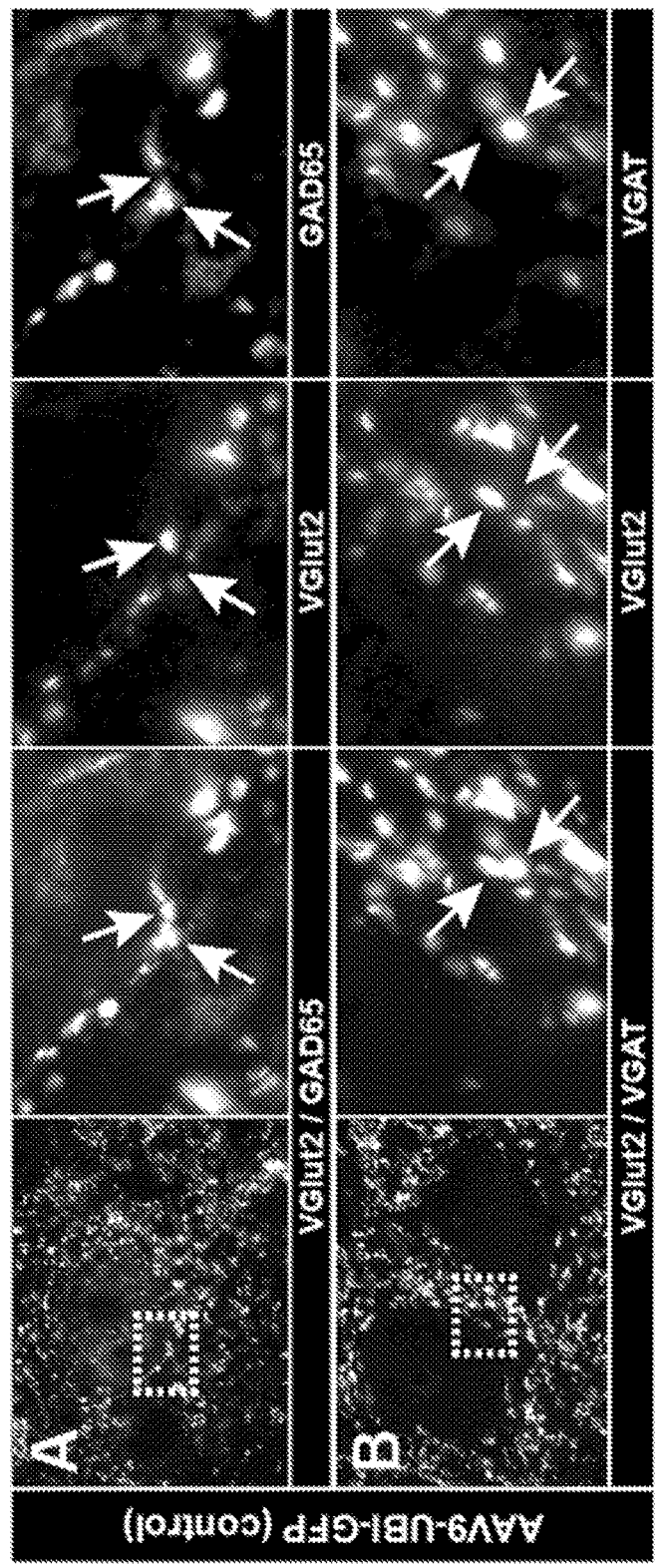

Bilateral (L2-L4) subpial AAV9-UBI-GAD65/VGAT delivery in the adult rat model of chronic muscle spasticity induced mixed inhibitory-excitatory neurotransmitter phenotype in lumbar excitatory interneurons. As shown in FIGS. 9C and 9D, the appearance of mixed neurotransmitter phenotype in spinal interneurons, as evidenced by co-expression of GAD65 and VGAT in VGLUT2 terminals, was observed. However, no co-expression of GAD65 and VGAT in VGLUT2 terminals was seen in animals receiving control AAV9-UBI-GFP vector (FIGS. 9A and 9B).

In comparison to control vector-injected animals a highly significant ($p<0.01$) increase in GAD65, VGAT expression and in number of VGLUT1 and VGLUT2 terminals co-expressing GAD65 and VGAT in gray matter was measured in spastic rats receiving lumbar subpial injection of AAV9-UBI-GAD65/VGAT vector (Table 2). Thus, spinal subpial delivery of AAV9-UBI-GAD65/VGAT vector is highly effective in suppressing chronic muscle spasticity in the well-established rat model of spinal transection-induced hind limb spasticity. Thus, the mechanism of measured anti-spasticity effect is based on induction of mixed excitatory-inhibitory neurotransmitter phenotype in spinal excitatory interneurons and resulting suppression of otherwise exacerbated spastic EMG response.

TABLE 2

Quantitative analysis of GAD65 and VGAT expression

| | Lumbar Subpial AAV9 delivery | | | | | |
|---|---|---|---|---|---|---|
| Experimental Groups | GAD65 % Normalized Signal (Integrated Density) | VGAT % Normalized Signal (Integrated Density) | VGLUT1 + GAD65 | VGLUT1 + VGAT | VGLUT2 + GAD65 | VGLUT2 + VGAT |
| | | | Co-expressing Puncta (*$P < 0.01$) | | | |
| AAV9-GAD65/VGAT (n = 4: 6 sections/animal) | 208 ± 19* | 166 ± 25* | 14 ± 8* | 9 ± 3.4* | 245 ± 97* | 331 ± 67* |
| AAV9-GFP (n = 4; 6 sections/animal) | 100 ± 7 | 100 ± 15 | 2 ± 1 | 2 ± 0.9 | 1 ± 0.7 | 5 ± 1 |

Although the invention has been described with reference to the above examples, it will be understood that modifications and variations are encompassed within the spirit and scope of the invention. Accordingly, the invention is limited only by the following claims.

What is claimed is:

1. A method of treating neuropathic pain in a subject in need thereof, comprising subpial administration of a composition comprising: (i) a first viral vector comprising a polynucleotide sequence encoding GAD65, and (ii) a second viral vector comprising a polynucleotide encoding polynucleotide encoding VGAT, wherein expression of the GAD65 is under the control of a first tissue-specific promoter, and VGAT is under the control of a second tissue-specific promoter, thereby treating neuropathic pain in the subject.

2. The method of claim 1, wherein the first or second viral vector comprises an AAV serotype 9 or Anc80 capsid.

3. The method of claim 1, wherein the concentration of the nucleic acid construct in the composition is between about 0.1-2.0×10$^{13}$ gc/ml.

4. The method of claim 1, wherein the first or second viral vector carrier is selected from the group consisting of a lentiviral vector, an adenoviral vector (AV), or an adeno-associated vector (AAV).

5. The method of claim 4, wherein the first or second viral vector is an AAV selected from the group consisting of AAV2, AAV3, AAV4, AAV5, AAV6, AAV7, AAV8, AAV9, AAV rh8, AAVrh10, AAVrh33, AAV rh34, and AAV Anc80.

6. The method of claim 1, wherein the first or second tissue-specific promoter is selected from the group consisting of human ubiquitin promoter and human synapsin promoter.

7. The method of claim 1, wherein the polynucleotide encoding GAD65 is SEQ ID NO: 2 or 5.

8. The method of claim 1, wherein the polynucleotide encoding VGAT is SEQ ID NO: 4 or 6.

9. A method for treating neuropathic pain in a subject in need thereof by gene therapy, comprising subpially administering a composition comprising a therapeutically effective amount of a gene therapy construct comprising (i) a viral vector sequence; (ii) a GAD65 gene sequence; and (iii) a VGAT gene sequence under control of a tissue-specific promoter, and a pharmaceutically acceptable carrier, thereby treating neuropathic pain in the subject.

10. The method of claim 9, wherein the viral vector is selected from the group consisting of a lentiviral vector, an adenoviral vector (AV), or an adeno-associated vector (AAV).

11. The method of claim 10, wherein the viral vector is an AAV selected from the group consisting of AAV2, AAV3, AAV4, AAV5, AAV6, AAV7, AAV8, AAV9, AAV rh8, AAVrh10, AAVrh33, AAV rh34, and AAV Anc80.

12. The method of claim 9, wherein the gene therapy construct comprises SEQ ID NO: 2 and SEQ ID NO: 4.

13. The method of claim 9, wherein the tissue-specific promoter is selected from the group consisting of human ubiquitin promoter and human synapsin promoter.

14. The method of claim 9, wherein the composition comprises the gene therapy construct at a concentration of about $0.1\text{-}2.0\times10^{13}$ gc/ml.

15. A method for treating neuropathic pain in a subject in need thereof, comprising subpial administration of a first vector encoding GAD65 and a second vector encoding VGAT, thereby treating neuropathic pain in the subject.

16. The method of claim 15, wherein each of the first and second vectors are independently selected from the group consisting of a lentiviral vector, an adenoviral vector (AV), or an adeno-associated vector (AAV).

17. The method of claim 16, wherein each of the first and second vectors is an AAV independently selected from the group consisting of AAV2, AAV3, AAV4, AAV5, AAV6, AAV7, AAV8, AAV9, AAV rh8, AAVrh10, AAVrh33, AAV rh34, and AAV Anc80.

18. The method of claim 15, wherein the first vector comprises SEQ ID NO: 2 and wherein the second vector comprises SEQ ID NO: 4.

19. A nucleic acid construct comprising: a viral vector sequence, a GAD65 gene sequence, and a VGAT gene sequence under the control of a tissue-specific promoter.

20. The nucleic acid construct of claim 19, wherein the tissue-specific promoter is selected from the group consisting of human ubiquitin promoter and human synapsin promoter.

21. The nucleic acid construct of claim 19, wherein the viral vector is an adeno-associated viral (AAV) vector selected from the group consisting of AAV2, AAV3, AAV4, AAV5, AAV6, AAV7, AAV8, AAV9, AAV rh8, AAVrh10, AAVrh33, AAV rh34, and AAV Anc80.

* * * * *

UNITED STATES PATENT AND TRADEMARK OFFICE
CERTIFICATE OF CORRECTION

PATENT NO. : 11,707,535 B2
APPLICATION NO. : 16/638972
DATED : July 25, 2023
INVENTOR(S) : Martin Marsala, Atsushi Miyanohara and Takahiro Tadokoro It is certified that error appears in the above-identified patent and that said Letters Patent is hereby corrected as shown below:

In the Claims

At Column 49, Lines 48-49: replace "comprising a polynucleotide encoding polynucleotide encoding VGAT" with --comprising a polynucleotide encoding VGAT--

Signed and Sealed this
Eighth Day of October, 2024

Katherine Kelly Vidal
*Director of the United States Patent and Trademark Office*

SEQUENCE LISTING

<160> NUMBER OF SEQ ID NOS: 6

<210> SEQ ID NO 1
<211> LENGTH: 585
<212> TYPE: PRT
<213> ORGANISM: Homo sapiens

<400> SEQUENCE: 1

```
Met Ala Ser Pro Gly Ser Gly Phe Trp Ser Phe Gly Ser Glu Asp Gly
1               5                   10                  15

Ser Gly Asp Ser Glu Asn Pro Gly Thr Ala Arg Ala Trp Cys Gln Val
            20                  25                  30

Ala Gln Lys Phe Thr Gly Gly Ile Gly Asn Lys Leu Cys Ala Leu Leu
        35                  40                  45

Tyr Gly Asp Ala Glu Lys Pro Ala Glu Ser Gly Gly Ser Gln Pro Pro
    50                  55                  60

Arg Ala Ala Ala Arg Lys Ala Ala Cys Ala Cys Asp Gln Lys Pro Cys
65                  70                  75                  80

Ser Cys Ser Lys Val Asp Val Asn Tyr Ala Phe Leu His Ala Thr Asp
                85                  90                  95

Leu Leu Pro Ala Cys Asp Gly Glu Arg Pro Thr Leu Ala Phe Leu Gln
            100                 105                 110

Asp Val Met Asn Ile Leu Leu Gln Tyr Val Val Lys Ser Phe Asp Arg
        115                 120                 125

Ser Thr Lys Val Ile Asp Phe His Tyr Pro Asn Glu Leu Leu Gln Glu
```

-continued

```
                130                 135                 140
Tyr Asn Trp Glu Leu Ala Asp Gln Pro Gln Asn Leu Glu Glu Ile Leu
145                 150                 155                 160

Met His Cys Gln Thr Thr Leu Lys Tyr Ala Ile Lys Thr Gly His Pro
                165                 170                 175

Arg Tyr Phe Asn Gln Leu Ser Thr Gly Leu Asp Met Val Gly Leu Ala
                180                 185                 190

Ala Asp Trp Leu Thr Ser Thr Ala Asn Thr Asn Met Phe Thr Tyr Glu
                195                 200                 205

Ile Ala Pro Val Phe Val Leu Glu Tyr Val Thr Leu Lys Lys Met
210                 215                 220

Arg Glu Ile Ile Gly Trp Pro Gly Gly Ser Gly Asp Gly Ile Phe Ser
225                 230                 235                 240

Pro Gly Gly Ala Ile Ser Asn Met Tyr Ala Met Met Ile Ala Arg Phe
                245                 250                 255

Lys Met Phe Pro Glu Val Lys Glu Lys Gly Met Ala Ala Leu Pro Arg
                260                 265                 270

Leu Ile Ala Phe Thr Ser Glu His Ser His Phe Ser Leu Lys Lys Gly
                275                 280                 285

Ala Ala Ala Leu Gly Ile Gly Thr Asp Ser Val Ile Leu Ile Lys Cys
                290                 295                 300

Asp Glu Arg Gly Lys Met Ile Pro Ser Asp Leu Glu Arg Arg Ile Leu
305                 310                 315                 320

Glu Ala Lys Gln Lys Gly Phe Val Pro Phe Leu Val Ser Ala Thr Ala
                325                 330                 335

Gly Thr Thr Val Tyr Gly Ala Phe Asp Pro Leu Leu Ala Val Ala Asp
                340                 345                 350

Ile Cys Lys Lys Tyr Lys Ile Trp Met His Val Asp Ala Ala Trp Gly
                355                 360                 365

Gly Gly Leu Leu Met Ser Arg Lys His Lys Trp Lys Leu Ser Gly Val
                370                 375                 380

Glu Arg Ala Asn Ser Val Thr Trp Asn Pro His Lys Met Met Gly Val
385                 390                 395                 400

Pro Leu Gln Cys Ser Ala Leu Leu Val Arg Glu Glu Gly Leu Met Gln
                405                 410                 415

Asn Cys Asn Gln Met His Ala Ser Tyr Leu Phe Gln Gln Asp Lys His
                420                 425                 430

Tyr Asp Leu Ser Tyr Asp Thr Gly Asp Lys Ala Leu Gln Cys Gly Arg
                435                 440                 445

His Val Asp Val Phe Lys Leu Trp Leu Met Trp Arg Ala Lys Gly Thr
450                 455                 460

Thr Gly Phe Glu Ala His Val Asp Lys Cys Leu Glu Leu Ala Glu Tyr
465                 470                 475                 480

Leu Tyr Asn Ile Ile Lys Asn Arg Glu Gly Tyr Glu Met Val Phe Asp
                485                 490                 495

Gly Lys Pro Gln His Thr Asn Val Cys Phe Trp Tyr Ile Pro Pro Ser
                500                 505                 510

Leu Arg Thr Leu Glu Asp Asn Glu Glu Arg Met Ser Arg Leu Ser Lys
                515                 520                 525

Val Ala Pro Val Ile Lys Ala Arg Met Met Glu Tyr Gly Thr Thr Met
                530                 535                 540

Val Ser Tyr Gln Pro Leu Gly Asp Lys Val Asn Phe Phe Arg Met Val
545                 550                 555                 560
```

```
Ile Ser Asn Pro Ala Ala Thr His Gln Asp Ile Asp Phe Leu Ile Glu
            565                 570                 575

Glu Ile Glu Arg Leu Gly Gln Asp Leu
            580                 585
```

<210> SEQ ID NO 2
<211> LENGTH: 1803
<212> TYPE: DNA
<213> ORGANISM: Homo sapiens

<400> SEQUENCE: 2

```
atgtcccta tacatcacca tcaccatcac ctggttccgc gtggatccga agcttcgaat      60
tctggctttt ggtctttcgg gtcggaagat ggctctgggg attccgagaa tcccggcaca     120
gcgcgagcct ggtgccaagt ggctcagaag ttcacgggcg gcatcggaaa caaactgtgc     180
gccctgctct acggagacgc cgagaagccg gcggagagcg gcgggagcca accccgcgg      240
gccgccgccc ggaaggccgc ctgcgcctgc gaccagaagc cctgcagctg ctccaaagtg     300
gatgtcaact acgcgtttct ccatgcaaca gacctgctgc cggcgtgtga tggagaaagg     360
cccactttgg cgtttctgca agatgttatg aacattttac ttcagtatgt ggtgaaaagt     420
ttcgatagat caaccaaagt gattgatttc cattatccta atgagcttct ccaagaatat     480
aattgggaat tggcagacca accacaaaat ttggaggaaa ttttgatgca ttgccaaaca     540
actctaaaat atgcaattaa aacagggcat cctagatact tcaatcaact ttctactggt     600
ttggatatgg ttggattagc agcagactgg ctgacatcaa cagcaaatac taacatgttc     660
acctatgaaa ttgctccagt atttgtgctt ttggaatatg tcacactaaa gaaaatgaga     720
gaaatcattg ctggccagg gggctctggc gatgggatat tttctcccgg tggcgccata     780
tctaacatgt atgccatgat gatcgcacgc tttaagatgt cccagaagt caaggagaaa     840
ggaatggctg ctcttcccag gctcattgcc ttcacgtctg aacatagtca tttttctctc     900
aagaagggag ctgcagcctt agggattgga acagacagcg tgattctgat aaatgtgat      960
gagagaggga aaatgattcc atctgatctt gaaagaagga ttcttgaagc caaacagaaa    1020
gggtttgttc ctttcctcgt gagtgccaca gctgaaacca ccgtgtacgg agcatttgac    1080
ccctcttag ctgtcgctga catttgcaaa aagtataaga tctggatgca tgtggatgca    1140
gcttggggtg ggggattact gatgtcccga aacacaagt ggaaactgag tggcgtggag    1200
agggccaact ctgtgacgtg aatccacac aagatgatgg agtcccttt gcagtgctct    1260
gctctcctgg ttagagaaga gggattgatg cagaattgca accaaatgca tgcctcctac    1320
ctctttcagc aagataaaca ttatgacctg tcctatgaca ctggagacaa ggccttacag    1380
tgcggacgcc acgttgatgt ttttaaacta tggctgatgt ggagggcaaa ggggactacc    1440
gggtttgaag cgcatgttga taatgtttg gagttggcag agtatttata caacatcata    1500
aaaaaccgag aaggatatga gatggtgttt gatgggaagc ctcagcacac aaatgtctgc    1560
ttctggtaca ttcctccaag cttgcgtact ctggaagaca tgaagagag atgagtcgc     1620
ctctcgaagg tggctccagt gattaaagcc agaatgatgg agtatggaac cacaatggtc    1680
agctaccaac ccttgggaga caaggtcaat ttcttccgca tggtcatctc aaacccagcg    1740
gcaactcacc aagacattga cttcctgatt gaagaaatag aacgccttgg acaagattta    1800
taa                                                                  1803
```

<210> SEQ ID NO 3

<211> LENGTH: 525
<212> TYPE: PRT
<213> ORGANISM: Homo sapiens

<400> SEQUENCE: 3

```
Met Ala Thr Leu Leu Arg Ser Lys Leu Ser Asn Val Ala Thr Ser Val
1               5                   10                  15

Ser Asn Lys Ser Gln Ala Lys Met Ser Gly Met Phe Ala Arg Met Gly
            20                  25                  30

Phe Gln Ala Ala Thr Asp Glu Glu Val Gly Phe Ala His Cys Asp
        35                  40                  45

Asp Leu Asp Phe Glu His Arg Gln Gly Leu Gln Met Asp Ile Leu Lys
50                  55                  60

Ala Glu Gly Glu Pro Cys Gly Asp Glu Gly Ala Glu Ala Pro Val Glu
65                  70                  75                  80

Gly Asp Ile His Tyr Gln Arg Gly Ser Gly Ala Pro Leu Pro Pro Ser
                85                  90                  95

Gly Ser Lys Asp Gln Val Gly Gly Gly Glu Phe Gly Gly His Asp
            100                 105                 110

Lys Pro Lys Ile Thr Ala Trp Glu Ala Gly Trp Asn Val Thr Asn Ala
            115                 120                 125

Ile Gln Gly Met Phe Val Leu Gly Leu Pro Tyr Ala Ile Leu His Gly
130                 135                 140

Gly Tyr Leu Gly Leu Phe Leu Ile Ile Phe Ala Ala Val Cys Cys
145                 150                 155                 160

Tyr Thr Gly Lys Ile Leu Ile Ala Cys Leu Tyr Glu Glu Asn Glu Asp
                165                 170                 175

Gly Glu Val Val Arg Val Arg Asp Ser Tyr Val Ala Ile Ala Asn Ala
            180                 185                 190

Cys Cys Ala Pro Arg Phe Pro Thr Leu Gly Gly Arg Val Val Asn Val
        195                 200                 205

Ala Gln Ile Ile Glu Leu Val Met Thr Cys Ile Leu Tyr Val Val Val
210                 215                 220

Ser Gly Asn Leu Met Tyr Asn Ser Phe Pro Gly Leu Pro Val Ser Gln
225                 230                 235                 240

Lys Ser Trp Ser Ile Ile Ala Thr Ala Val Leu Leu Pro Cys Ala Phe
                245                 250                 255

Leu Lys Asn Leu Lys Ala Val Ser Lys Phe Ser Leu Leu Cys Thr Leu
            260                 265                 270

Ala His Phe Val Ile Asn Ile Leu Val Ile Ala Tyr Cys Leu Ser Arg
        275                 280                 285

Ala Arg Asp Trp Ala Trp Glu Lys Val Lys Phe Tyr Ile Asp Val Lys
290                 295                 300

Lys Phe Pro Ile Ser Ile Gly Ile Ile Val Phe Ser Tyr Thr Ser Gln
305                 310                 315                 320

Ile Phe Leu Pro Ser Leu Glu Gly Asn Met Gln Gln Pro Ser Glu Phe
                325                 330                 335

His Cys Met Met Asn Trp Thr His Ile Ala Ala Cys Val Leu Lys Gly
            340                 345                 350

Leu Phe Ala Leu Val Ala Tyr Leu Thr Trp Ala Asp Glu Thr Lys Glu
        355                 360                 365

Val Ile Thr Asp Asn Leu Pro Gly Ser Ile Arg Ala Val Val Asn Ile
370                 375                 380

Phe Leu Val Ala Lys Ala Leu Leu Ser Tyr Pro Leu Pro Phe Phe Ala
```

```
                385                 390                 395                 400
Ala Val Glu Val Leu Glu Lys Ser Leu Phe Gln Glu Gly Ser Arg Ala
                405                 410                 415

Phe Phe Pro Ala Cys Tyr Ser Gly Asp Gly Arg Leu Lys Ser Trp Gly
            420                 425                 430

Leu Thr Leu Arg Cys Ala Leu Val Val Phe Thr Leu Met Ala Ile
            435                 440                 445

Tyr Val Pro His Phe Ala Leu Leu Met Gly Leu Thr Gly Ser Leu Thr
        450                 455                 460

Gly Ala Gly Leu Cys Phe Leu Leu Pro Ser Leu Phe His Leu Arg Leu
465                 470                 475                 480

Leu Trp Arg Lys Leu Leu Trp His Gln Val Phe Phe Asp Val Ala Ile
                485                 490                 495

Phe Val Ile Gly Gly Ile Cys Ser Val Ser Gly Phe Val His Ser Leu
                500                 505                 510

Glu Gly Leu Ile Glu Ala Tyr Arg Thr Asn Ala Glu Asp
            515                 520                 525
```

<210> SEQ ID NO 4
<211> LENGTH: 2581
<212> TYPE: DNA
<213> ORGANISM: Homo sapiens

<400> SEQUENCE: 4

```
gctcgcgccc cgcggcagct ccgcagtgca ctagccacca ccgccgccgc cgccgctccg    60
ccagacctgc tgccagcttg cccggtccag ccctgagaga gcctcgaacg ccagctgcga   120
gggtcatgag ccagagagcc ccggggcgcc gcgcggagag caagcggaga tagcgacttt   180
gcgcccccca gccctcgcct tcttgcatcg cgttccccgc atcctcgggt ccttctgtcc   240
tttccgctgt ccccaccgcc gccatggcca ccttgctccg cagcaagctg tccaacgtgg   300
ccacgtccgt gtccaacaag tcccaggcca agatgagcgg catgttcgcc aggatgggtt   360
tcaggcggc acggatgag gaggcggtgg gcttcgcgca ttgcgacgac ctcgactttg   420
agcaccgcca gggcctgcag atggacatcc tgaaagccga gggagagccc tgcggggacg   480
agggcgctga agcgcccgtc gagggagaca tccattatca gcgaggcagc ggagctcctc   540
tgccgccctc cggctccaag gaccaggtgg gaggtggtgg cgaattcggg ggccacgaca   600
agcccaaaat cacggcgtgg gaggcaggct ggaacgtgac caacgccatc cagggcatgt   660
tcgtgctggg cctaccctac gccatcctgc acggcggcta cctggggttg tttctcatca   720
tcttcgccgc cgttgtgtgc tgctacaccg gcaagatcct catcgcgtgc ctgtacgagg   780
agaatgaaga cggcgaggtg gtgcgcgtgc gggactcgta cgtggccata gccaacgcct   840
gctgcgcccc gcgcttccca acgctgggcg gccgagtggt gaacgtagcg cagatcatcg   900
agctggtgat gacgtgcatc ctgtacgtgg tggtgagtgg caacctcatg tacaacagct   960
tcccgggagct gccccgtgtcg cagaagtcct ggtccattat cgccacggcc gtgctgctgc  1020
cttgcgcctt ccttaagaac ctcaaggccg tgtccaagtt cagtctgctg tgcactctgg  1080
cccacttcgt catcaatatc ctggtcatag cctactgtct atcgcgggcg cgcgactggg  1140
cctgggagaa ggtcaagttc tacatcgacg tcaagaagtt ccccatctcc attggcatca  1200
tcgtgttcag ctacacgtct cagatcttcc tgccttcgct ggagggcaat atgcagcagc  1260
ccagcgagtt ccactgcatg atgaactgga cgcacatcgc agcctgcgtg ctcaagggcc  1320
tcttcgcgct cgtcgcctac ctcacctggg ccgacgagac caaggaggtc atcacggata  1380
```

```
acctgcccgg ctccatccgc gccgtggtca acatctttct ggtggccaag gcgctgttgt    1440
cctatcctct gccattcttt gccgctgtcg aggtgctgga gaagtcgctc ttccaggaag    1500
gcagccgcgc cttttttccg gcctgctaca gcggcgacgg gcgcctgaag tcctgggggc    1560
tgacgctgcg ctgcgcgctc gtcgtcttca cgctgctcat ggccatttat gtgccgcact    1620
tcgcgctgct catgggcctc accggcagcc tcacgggcgc cggcctctgt ttcttgctgc    1680
ccagcctctt tcacctgcgc ctgctctggc gcaagctgct gtggcaccaa gtcttcttcg    1740
acgtcgccat cttcgtcatc ggcggcatct gcagcgtgtc cggcttcgtg cactccctcg    1800
agggcctcat cgaagcctac cgaaccaacg cggaggacta gggcgcaagg gcgagccccc    1860
gccgcgcttc tgcgctctct cccttctccc ctcaccccgc ccccaccagc ccagtgcgcc    1920
ctgccgccgc gcttgggagg ccaagcttta acatctctg gttcctagtt tctgattatt    1980
cggggatggg gggatggga gggacaggg attcacgatc catcgcgtct gcgtttctgt    2040
tgtcctttct tttccacaac accctggttt tgggggagg cggggtgcat ttgcgggcag    2100
ggttctctgt ccttccaagt ggggccccga cactttggtt ccagtcatcg aggggttgg    2160 gaagggaggg agaggggcg cagctcgcag gcgtggcaac ttgaccttgg gggaatattt    2220
cacatccatc cagagctcgg aatctacagc gtccagccat ttccagcaag agcgcttccc    2280
attccggaga cgtttcaacc ctgcagcggg aaaggctgac tgggaaatcc attttgggtg    2340
ggcaatttcc ttcaacgaag ccggaaggcg agaagccgcg gcggggccag cttgcctgcc    2400
ggttttcagg aatctaaact ctcatcttgt gcaatttatc aggtgtggaa ctgttctact    2460
gtgcgtgtgg tgtgctcgtg gtgaataaga tgaaatgtat atcagaaaaa aatctatctc    2520
taatttagag tgcggtacat aattatatcc gcaaataaag aagagacaaa ggctaaaaaa    2580
a                                                                    2581

<210> SEQ ID NO 5
<211> LENGTH: 1966
<212> TYPE: DNA
<213> ORGANISM: Rattus norvegicus

<400> SEQUENCE: 5
gggcgtgcgg ggtcgagccg aagcagcttg cccgcagcca ctcggaggcg accagcgcca     60
gactagcaga acccatggca tctccgggct ctggcttttg gtccttcgga tctgaagatg    120
gctctgggga tcctgagaac ccgggaacag cgagagcctg gtgccaggtg gcccaaaagt    180 tcacgggcg catcggaaac aagctatgcg ctctgctcta cggagactct gagaagccag    240
cagagagcgg cgggagcgtg acctcgcggg ccgccactcg gaaggtcgcc tgcacctgtg    300
accaaaaacc ctgcagctgc cccaaaggag atgtcaatta tgcacttctc cacgcaacag    360
acctgctgcc agcctgtgaa ggagaaaggc ccactctcgc atttctgcaa gatgtaatga    420 acatttgct tcagtacgtg gtgaaaagtt ttgatagatc aactaaagtg attgatttcc    480
attaccccaa tgagcttctt caagagtata attgggaatt ggcagaccaa ccgcaaaatc    540
tggaggaaat tttgacgcac tgccaaacaa ctctaaaata tgcgattaaa acagggcatc    600
cccgatattt taatcagctg tctaccggat tggatatggt tggattagca gcagattggt    660
tgacatcaac agcaaacacg aacatgttta cctatgagat cgcccctgta tttgtactac    720
tggaatatgt gacactaaag aaaatgaggg aaatcattgg ctggccagga ggctctggcg    780
atggaatctt ttctcctggt ggtgccatct ccaacatgta cgccatgctc attgcccgct    840
```

-continued

| | |
|---|---:|
| ataagatgtt tccagaagtc aaggaaaagg ggatggcggc ggtgcccagg ctcatcgcat | 900 |
| tcacgtcaga gcatagtcac ttttctctca agaagggagc tgcagccttg gggatcggaa | 960 |
| cagacagcgt gattctgatt aaatgtgatg agagagggaa aatgatccca tctgaccttg | 1020 |
| aaagaagaat ccttgaagtc aaacagaaag gatttgttcc tttcctggtg agtgccacag | 1080 |
| ctggaaccac tgtgtacggg gcttttgatc ctctcttggc tgtagctgac atctgcaaaa | 1140 |
| aatataagat ctggatgcat gtggatgctg cttggggtgg agggttactg atgtctcgga | 1200 |
| aacacaagtg gaagctgaac ggtgtggaga gggccaactc tgtgacatgg aatccccaca | 1260 |
| agatgatggg tgtccccttg caatgttcgg ctctcctggt cagagaggag ggactgatgc | 1320 |
| agagctgcaa ccagatgcat gcttcctacc tctttcagca agataagcac tatgacctgt | 1380 |
| cctatgacac gggagacaag gccttgcagt gtggacgcca cgtcgatgtc tttaaattat | 1440 |
| ggctcatgtg gagagcaaag gggactactg gatttgaagc tcacattgat aagtgtttgg | 1500 |
| agctggcaga gtatttatac aatatcatta aaaaccgaga aggatatgaa atggtgttcg | 1560 |
| atgggaagcc tcagcacaca aatgtctgct tctggttttgt acctcctagt ttgcgagttc | 1620 |
| tggaagacaa tgaagagaga atgagccgcc tctcaaaggt ggcgccagtg attaaagcca | 1680 |
| gaatgatgga gtatgggacc acaatggtca gctaccaacc cttaggagat aaggtcaact | 1740 |
| tcttccgcat ggtcatctca aaccctgcag caactcacca agacattgac ttcctcattg | 1800 |
| aagaaatcga acgcctggga caagatttgt aatcactttg ctcaccaaac tttcagttct | 1860 |
| ctaggtagac agctaagttg tcacaaactg tgtaaatgta tttgtagttt gttccagagt | 1920 |
| aattctattt ctatatcgtg gtgtcacagt agagtccagt ttaaaa | 1966 |

<210> SEQ ID NO 6
<211> LENGTH: 2392
<212> TYPE: DNA
<213> ORGANISM: Rattus norvegicus

<400> SEQUENCE: 6

| | |
|---|---:|
| agcggagata gcggcccttg ctgccttgac gcgcgcccgc cgcgtcccca gacccttctg | 60 |
| tccttttctc ccgccccgcc gccgccatgg ccaccctgct ccgcagcaag ctgaccaacg | 120 |
| tggccacctc tgtgtccaac aagtcccagg ccaaggtgag cggcatgttc gccaggatgg | 180 |
| ggtttcaggc ggccacggat gaggaggcgg tgggcttcgc gcactgcgac gatctcgact | 240 |
| tgagcaccg ccagggcctg cagatggaca tcctgaaatc ggaaggcgag ccctgcgggg | 300 |
| acgagggcgc agaacctccc gtcgaggag acattcatta tcagcgcggc ggcgctcccc | 360 |
| tgccacccte gggctccaag gaccaggccg tgggagctgg tggggagttc gggggtcacg | 420 |
| acaaacccaa gatcacggcg tgggaagcgg gctggaacgt gacaaacgcc attcagggca | 480 |
| tgttcgtgct gggtctaccc tacgccatcc tccacggcgg ctacctgggg ttgttcctca | 540 |
| tcatcttcgc cgcggtggtg tgctgctaca ccggcaagat cctcatcgcg tgcctgtacg | 600 |
| aggagaacga agatggtgag gtggtgcgcg tgagggactc gtatgtggcc atagctaacg | 660 |
| cgtgctgcgc tcctcgattc cccacgctgg gcggccgcgt ggtcaatgtg gcccagatca | 720 |
| tcgagctggt gatgacgtgt atcttgtacg tagtggtgag cggcaacctc atgtacaaca | 780 |
| gtttcccggg gctgcccgtg tcgcagaagt cctggtccat catagccacg gcggtgctgc | 840 |
| tgccctgcgc cttcctgaag aatctcaagg ccgtgtccaa gttcagtctg ctgtgcacgc | 900 |
| tggcccactt cgtcatcaac atcctggtca tcgcctactg tctctcgcgc gcgcgtgact | 960 |
| gggcctggga gaaggtgaag ttctacatcg acgtcaagaa gtttcctatc tccatcggca | 1020 |

```
tcatcgtgtt cagctacacg tcgcagatct tcctgccctc gctcgaaggc aacatgcagc    1080
agcccagcga attccactgc atgatgaact ggacacacat cgccgcctgc gtgctcaagg    1140
gtctcttcgc gctcgtcgcc tacctcacct gggccgacga gaccaaggaa gtcatcacgg    1200
ataacctgcc cggttccatc cgcgccgtgg tcaacatctt cctggtggcc aaggcgctgc    1260
tgtcctaccc gttgcccttc ttcgcggccg tcgaagtgct ggagaagtct ctcttccagg    1320
aaggcagtcg tgccttcttc cccgcctgct acggtggcga cggtcgcctt aagtcctggg    1380
ggctgacgct gcgctgcgcg ctggtggtct tcacgctgct catggccatc tacgtgccac    1440
acttcgcgct gctcatgggc ctcacgggca gcctcacggg agccgcctc tgcttcctgc     1500 tgcccagcct cttccacttg cgtcttctct ggcgcaagct gctgtggcac caggtcttct    1560
tcgatgtggc catcttcgtc atcggcggca tctgcagcgt gtccggcttc gtgcattcac    1620
tcgagggcct catcgaggcc taccgaacca acgcagagga ctaggggcg gggaccctgc     1680 ccccagctcc ctccccgccc accccactc cccttatcc ccgccccaa ccccaccc         1740 cagcccctg cgcaaccacg ctggggaggc cgagctttaa acacctccgg ttcctagttg     1800
ctgattattc ggggaccggg cggggagg aggggatag acatccaagg tccactgcgt       1860
ctgcgtttct gtcgttcttt ctattccaca tcgtcctgat ttgggggag ggagcagagc     1920 gtataagtga agggtatttt ctgtccttcc tagaacaccc accaccacca ccaccaaact    1980
ttggctccag tcaatgttag gggtgggaag ggaggggaa agggaacacg cagttcgcag     2040
gctcggaaac ttgaccttgg gggtgggtg ggggacattt cacagccatt cagtgcttgg     2100
aatctactgc gtccagccat ttccagcaag agcgctcccc atgccctaga catttcaacc    2160
ttgaggcctg aaaggctgac cgggaaatcc atttcgggca ggcgacttcc ctctggagaa    2220
gccgcggcag gggcccccgt ttgcctgccg gttttcagga acccaaactc atcttgtgca    2280
atgtatccgg ttgtggaact gtatactgtg cgtgtggtgt gctcgtggtg aataagatga    2340
aatgtatatc agaaaaaatc tatctctaat ttagagtgcg gtgcctcgtg cc            2392
```